(12) United States Patent
Christofidou-Solomidou et al.

(10) Patent No.: US 11,197,876 B2
(45) Date of Patent: Dec. 14, 2021

(54) EFFECTS OF LGM2605 ON A PRIMATE MODEL OF ASTHMA

(71) Applicants: THE TRUSTEES OF THE UNIVERSITY OF PENNSYLVANIA, Philadelphia, PA (US); The Regents of the University of California, Oakland, CA (US)

(72) Inventors: Melpo Christofidou-Solomidou, Eagleville, PA (US); Angela Haczku, Davis, CA (US)

(73) Assignees: THE TRUSIEES OF THE UNIVERSITY OF PENNSYLVANIA, Philadelphia, PA (US); THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 16/153,494

(22) Filed: Oct. 5, 2018

(65) Prior Publication Data

US 2019/0038652 A1   Feb. 7, 2019

Related U.S. Application Data

(63) Continuation-in-part of application No. 15/315,349, filed as application No. PCT/US2015/033501 on Jun. 1, 2015, now abandoned.

(60) Provisional application No. 62/005,330, filed on May 30, 2014, provisional application No. 62/101,293, filed on Jan. 8, 2015.

(51) Int. Cl.
| | | |
|---|---|---|
| *A61K 31/7032* | (2006.01) | |
| *A61P 39/00* | (2006.01) | |
| *A61P 11/06* | (2006.01) | |
| *A61K 9/00* | (2006.01) | |

(52) U.S. Cl.
CPC ........ *A61K 31/7032* (2013.01); *A61K 9/0053* (2013.01); *A61P 11/06* (2018.01); *A61P 39/00* (2018.01)

(58) Field of Classification Search
None
See application file for complete search history.

(56) References Cited

U.S. PATENT DOCUMENTS

| | | |
|---|---|---|
| 5,705,618 A | 1/1998 | Westcott et al. |
| 10,045,951 B2 | 8/2018 | Christofidou-Solomidou |
| 10,449,224 B2 | 10/2019 | Christofidou-Solomidou |
| 10,966,995 B2 * | 4/2021 | Christofidou-Solomidou ............ A61K 31/05 |
| 2010/0239696 A1 | 9/2010 | Solomidou |
| 2011/0135641 A1 | 6/2011 | Senberg et al. |
| 2014/0308379 A1 | 10/2014 | Christofidou-Solomidou |

FOREIGN PATENT DOCUMENTS

| | | |
|---|---|---|
| WO | WO-2008/147563 | 12/2008 |
| WO | WO-2014/200964 | 12/2014 |

OTHER PUBLICATIONS

Mishra et al. "Synthesis and antioxidant evaluation of (s,S)- and (R, R)-secoisolariciresinol diglucosides (SDgs)." Bioorg Med Chem Lett Aug. 2, 2013 (Aug. 2, 2013), vol. 23, No. 19, pp. 5325-5328. entire document.

Machlin et al. "Free radical tissue damage; protective role of antiocidant nutrients," FASEB J. Dec. 1, 1987 (Dec. 1, 1987), vol. 1, No. 6, pp. 441-445, entire document.

Huang et al. "Natural phenolic compounds from medicinal herbs and dietary plants; potential use for cancer prevention," Nutr Cancer, Dec. 29, 2009 (Dec. 29, 2009), vol. 62, No. 1, pp. 1-20, entire document.

AYELIA et al., "Cytostatic inhibition of cancer cell growth by lignan secoisolariciresinol diglucoside"—Nutrition Research, Elsevier Inc., Nov. 2010, vol. 30, No. 11, pp. 762-769.

Chen et al., "Flaxseed and Pure Secoisolariciresinol Digulcoside, but Not Flaxseed Hull, Reduce Human Breast Tumor Growth (MCF-7) in Athymio Mice1,2"—The Journal of Nutrition Sep. 23, 2009, vol. 139, No. 11 pp. 2061-2066.

Christofidou-Solomidou et al., "Radioprotective Role in Lung of the Flaxseed Lignan Complex Enriched in the Phenolic Secoisolariciresinol Diglucoside (SDG)"—Radiat Res. Dec. 2012: 178(6): pp. 568-580.

Hongyan et al., "Lignans are involved in the antitumor activity of wheat bran in colon cancer SW480 cells"—J. Nutr. (2005) 135: pp. 598-602.

Lee et al., "Dietary Flaxseed Prevents Radiation-induced Oxidative Lung Damage, Inflammation and Fibrosis in a Mouse Model of Thoracic Radiation Injury"—Cancer Biol & Ther. Jan. 2009; 8(1): 47-53.

Li et al., "Dietary supplementation with secoisolariciresinol diglycoside 9SDG) reduces experimental metastasis of melanoma cells in mice"—Cancer Letters, Jul. 19, 1999, vol. 142, No. 1, pp. 91-96.

Mishra et al., "Novel Synthetic (S,S) and (R,R)-Secoisolariciresinol Digulcosides 9SDGs) Protect Naked Plasmid and Genomic DNA From Gamma Radiation Damage"—Radiation Research (2014), 182(1), pp. 102-110.

Moree et al., "Secoisolariciresinol Diglucoside—A Phytoestrogen Nutraceutical of Flaxseed: Synthesis and Evaluation of Antioxidant Potency"—Free Radicals and Antioxidants, Oct. 1, 2011, vol. 1, Nov. 4, pp. 31-38.

(Continued)

*Primary Examiner* — Traviss C Mcintosh, III
(74) *Attorney, Agent, or Firm* — Mark S. Cohen; Pearl Cohen Zedek Latzer Baratz LLP

(57) ABSTRACT

The invention provides compositions and methods for treating asthma in a subject in need thereof comprising administering chemically synthesized secoisolariciresinol diglucoside (SDG), and in particular, a racemic mixture of the SDG (LGM2605), stereoisomers thereof, metabolites thereof, and analogs thereof. Also provided are methods for treating or preventing ozone-induced damage in a subject in need thereof.

25 Claims, 9 Drawing Sheets

(56) References Cited

OTHER PUBLICATIONS

Pietrofesa et al., "Radiation mitigating properties of the lignan component in flaxseed"—BMC Cancer, Biomed Central, London, GB, Apr. 4, 2013, vol. 13, No. 1, p. 179.

Thompson et al., "Antitumorigenic effect of a mammalian lignan precursor from flaxseed"—Nutrition and Cancer 1996, vol. 26 No. 2, pp. 159-165.

Partial Supplementary EP Search Report dated Dec. 19. 2017 for EP Appln No. 15799095.3.

Bambagiotti-Alberti, et al. "Investigation of mammalian lignan precursors in flax seed: First evidence of secoisolariciresinol diglucoside in two isomeric forms by liquid chromatography/mass spectrometry." Rapid communications in mass spectrometry 8.12 (1994): 929-932.

Bénard, et al. "Prognostic value of FDG PET imaging in malignant pleural mesothelioma." The Journal of Nuclear Medicine 40.8 (1999): 1241.

Brown et al. "World Mineral Production 2004-2008" 2010 World mineral production 2004-2008. Nottingham, UK, British Geological Survey, 120 pp.

Carbone et al., "Molecular pathways: targeting mechanisms of asbestos and erionite carcinogenesis in mesothelioma." Clinical Cancer Research 18.3 (2012): 598-604.

Eklund, et al. "Synthesis of (-)-matairesinol, (-)-enterolactone and (-)-enterodiol from the natural lignan hydroxymatairesinol." Organic letters 5.4 (2003): 491-493.

Hong et al., "Recent advances in chemoprevention of cancer." Science 278.5340 (1997): 1073-1077.

Li et al., "Inhibition of secoisolariciresinol diglucoside on lung cancer cell line A549 and its mechanism". Chemical Abstracts Service, Columbus Ohio, Retrieved from STN, Database Accession No. 2011:728760.

Machlin et al., "Free radical tissue damage; protective role of antioxidant nutrients". FASEB J. Dec. 1, 1987, vol. 1, No. 6, pp. 441-445.

Neri et al. "Chemoprevention of asbestos-linked cancers: a systematic review." Anticancer research 32.3 (2012): 1005-1013.

Pendyala, et al. "Phase I/pharmacodynamic study of N-acetylcysteine/ oltipraz in smokers: early termination due to excessive toxicity." Cancer Epidemiology and Prevention Biomarkers 10.3 (2001): 269-272.

Qu et al., Lignans are Involved in the Antitumor Activity of Wheat Bran in Colon Cancer SW480 Cells 1,2 (2004), pp. 598-602.

Sadiq et al., "Secoisolariciresinol Diglucoside—A Phytoestrogen Nutraceutical of Flaxseed: Synthesis and Evaluation of Antioxidant Potency". Free Radicals and Antioxidants, vol. 1, No. 4, Oct. 1, 2011, pp. 31-38.

Sterman et al. "Advances in the diagnosis, evaluation, and management of malignant pleural mesothelioma." Respirology 10.3 (2005): 266-283.

Sterman et al. "Long-term follow-up of patients with malignant pleural mesothelioma receiving high-dose adenovirus herpes simplex thymidine kinase/ganciclovir suicide gene therapy." Clinical cancer research 11.20 (2005): 7444-7453.

Sterman et al., "Advances in the treatment of malignant pleural mesothelioma." Chest 116.2 (1999): 504-520.

Tan et al. "Dietary chemoprevention strategies for induction of phase II xenobiotic-metabolizing enzymes in lung carcinogenesis: a review." Lung Cancer 65.2 (2009): 129-137.

* cited by examiner

EFFECTS OF LGM2605 ON A PRIMATE MODEL OF ASTHMA

CROSS-REFERENCE TO RELATED APPLICATIONS

This application is continuation-in-part application of U.S. patent application Ser. No. 15/315,349, filed Nov. 30, 2016, which is a National Phase Application of PCT International Application No. PCT/US2015/033501, International Filing Date Jun. 1, 2015, claiming priority of U.S. Provisional Patent Application(s) No(s). 62/005,330, filed May 30, 2014, and 62/101,296, filed Jan. 8, 2015, which are hereby incorporated by reference.

GOVERNMENT INTEREST STATEMENT

This invention was made with government support under grant numbers CA133470, ES013508, AI081251 and CA016520, ES023720, CA180548, CA133470, awarded by the National Institutes of Health. The government has certain rights in the invention.

FIELD OF THE INVENTION

Provided herein are compositions and methods for treating asthma in a subject in need thereof using chemically synthesized secoisolaricirecinol diglucoside (SDG), and in particular, a racemic mixture of the SDG (which is referred to herein as LGM2605), stereoisomers thereof, metabolites thereof, and analogs thereof. Also provided are methods for treating or preventing ozone-induced damage in a subject in need thereof.

BACKGROUND OF THE INVENTION

Ozone (also referred to herein as "$O_3$") is a toxic air pollutant that, when inhaled acutely in mice and humans, causes bronchoalveolar lavage (BAL) inflammation and reduced lung function (airways hyperreactivity; "AHR"). These results were observed in non-human primate rhesus macaques (*Macaca mulatta*), a species that displays remarkable sensitivity to $O_3$, similar to humans Acute $O_3$ inhalation alters redox balance and causes oxidative stress in the lung. An oxidative lung microenvironment prompts hyperactive innate immune responses that favor activation of dendritic cells (DCs) and adaptive T lymphocytes. It has been demonstrated previously that group 2 innate lymphoid cells (ILC2s) were required and sufficient for $O_3$-induced AHR and BAL neutrophilia and eosinophilia in mice. In the absence of the pulmonary immunoregulatory protein surfactant protein-D (SP-D), ILC2 activation was enhanced (unpublished) and BAL inflammation was heightened after $O_3$ inhalation. Oxidative damage to the quaternary structure of SP-D promoted by $O_3$ inhalation reduced its immunosuppressive function. $O_3$ inhalation activated pulmonary DCs and trapped them in the lung, which was enhanced in the absence of SP-D. As DCs link innate and adaptive immunity, retention of these cells in response to $O_3$ may increase allergic sensitization and contribute to lung injury. In humans exposed acutely to $O_3$, increased numbers of activated (CD25+) CD4+ T cells were recovered from the BAL, suggesting that activation of innate immunity led to adaptive responses. Taken together, prior studies demonstrate that innate immune cells and immunoregulatory proteins are highly sensitive to $O_3$ inhalation.

Chronic inflammation and AHR are the hallmarks of asthma, thus $O_3$ exposure can be utilized in the laboratory to study the initiation of pulmonary inflammation and AHR. The mainstream drugs of choice for severe asthma and airway inflammation (glucocorticoids) have no effect in steroid-resistant patients. Development of novel compounds that reduce airway inflammation and improve lung function in a glucocorticoid receptor-independent mechanism are desperately needed in the clinic. LGM2605 is a non-toxic, synthetic lignan secoisolariciresinol diglucoside shown to have robust anti-inflammatory effects independent of the glucocorticoid receptor. Indeed, this novel compound is thought to act via anti-oxidative induction of nuclear factor-E2 related factor 2 (Nrf2) expression, free radical scavenging, inhibition of myeloperoxidase activity, and impaired NLRP3 inflammasome and NF-κB activation. Expression of Nrf2 in the lung reduced oxidative stress and maintains the proper Th1/Th2 balance. Absence of Nrf2 lead to reduced antioxidant enzyme expression and enhanced Th2 cytokine expression in the lung during bleomycin- and allergen-induced inflammation. Pharmacologic enhancement of Nrf2 during allergen-induced inflammation reduced inflammation and AHR. Similar to mice lacking SP-D, $Nrf2^{-/-}$ mice were highly susceptible to $O_3$-induced lung damage and inflammation.

Ionizing radiation produces a wide range of deleterious effects in living organisms. Humans are exposed to radiation as an occupational hazard, during diagnostic and therapeutic radiographic procedures, when using electronic devices, from background radiation of nuclear accidents, during air and space travel, as well as from prolonged exposure to the sun (e.g., sun bathers or outdoor workers). Exposure to natural radiation can occur in many forms: natural resources such as air, water, and soil may become contaminated when they come in contact with naturally-occurring, radiation-emitting substances (radionuclides); radon is one such common source of natural radiation. Current global developments have additionally established terrorism as a dangerous means by which potentially large numbers of people can be exposed to lethal amounts of radiation. It is, therefore, of high importance to identify agents that can be administered before and during exposure to radiation (i.e., radioprotective agents), and as treatment after radioactive exposure (i.e., radiation mitigators).

In addition, lung cancer is the leading cause of cancer mortality in the United States. Despite novel targeted therapeutic agents, improved staging and surgical techniques, and increased utilization of concomitant chemoradiation therapy for locally advanced lung cancer there has only been a minimal decrease of overall mortality rates (Tan & Spivack (2009) *Lung Cancer* 65:129-137). Cancer chemoprevention has been defined as the use of dietary and pharmacological intervention with specific natural or synthetic agents designed to prevent, suppress, or reverse the process of carcinogenesis before the development of malignancy (Hong & Sporn, (1997). *Science* 278:1073-1077). One strategy for lung cancer chemoprevention focuses on the use of agents that modulate the metabolism and disposition of tobacco, environmental and other carcinogens through upregulation of detoxifying phase II enzymes. Many synthetic and naturally occurring compounds are known to induce the expression of phase II enzymes. There have been numerous reports that support the idea that Nrf2/ARE-regulated phase II enzyme induction is a highly effective strategy for reducing susceptibility to carcinogens. We have data to show that flaxseed (FS) and its main lignan SDG, both from enrichment of the natural material and synthetically derived, are effective lung cancer chemoprevention agents in a mouse model of chemical carcinogen-induced lung cancer.

Approximately 85% of lung cancer is caused by smoking. Major lung carcinogens in tobacco smoke are polycyclic aromatic hydrocarbons, typified by benzo[a]pyrene (BaP). Until better treatments are developed, the best hope for decreasing deaths will be prevention through screening, smoking cessation, or chemoprevention. Chemopreventive agents must be given for prolonged periods of time in large numbers of exposed, but relatively healthy subjects. They must be safe, non-toxic, palatable, and ideally, affordable. A number of chemopreventive agents have been studied in lung cancer, however none have met these criteria. One of the most promising approaches is upregulation of Phase II anti-oxidant and detoxifying enzymes. Unfortunately, the Phase II enzyme activators tested in patients to date, such as Oltipraz or Sulforophane, have proven to be unacceptably toxic (Pendyala et al. (2001). *Cancer Epidemiol Biomarkers Prev* 10:269-272). Safe, non-toxic chemopreventive agents that are effective in preventing the oxidative stress and the DNA damage induced by lung carcinogens in tobacco smoke are thus desperately needed.

Another well-known environmental carcinogen is asbestos, which refers to a group of naturally occurring hydrated fibrous silicate fibers used commercially for insulation. It has now been clearly established in both animal models and in patients that asbestos fiber inhalation can lead to neoplastic diseases such as malignant mesothelioma (MM) and lung cancer (Carbone & Yang (2012). *Clin Cancer Res* 18:598-604; Neri et al. (2012). *Anticancer Res* 32:1005-1013), as well as pulmonary fibrosis. MM is a highly aggressive cancer that arises from the mesothelial cells of the pleura and peritoneum with a median survival of about 1 year (Sterman et al. (2005). Clin Cancer Res 11, 7444-7453; Sterman et al. (1999). Chest 116, 504-520; Benard et al. (1999). J Nucl Med 40, 1241-1245). Current therapies, other than surgery in very early disease, are not curative (Sterman & Albelda (2005). Respirology 10, 266-283). Presently, MM causes about 3,000 deaths per year in the US and an additional 5,000 deaths/year in Western Europe.

Although asbestos use has been restricted in many western countries, it is still used in many countries around the world and it is estimated that more than 2 million tons were mined in 2008 (Survey, B. G. (2010). World Mineral Production 2004-08. Nottingham, UK, British Geological Survey). There will thus likely be a dramatic increase in MM cases in the third world (especially in India) where the use of asbestos has increased with few precautions taken. However, even in the developed world, important exposures still exist. These include many types of occupations that expose workers to pre-existing asbestos (i.e. plumbers, pipefitters, insulators, insulation removal, etc.) as well as superfund asbestos hazardous waste sites. There are also environmental and domestic exposures. For example, there is an increased risk of MM in areas where mining or asbestos factories have closed.

A major issue in the link between asbestos and cancer is that inhaled asbestos fibers can persist in the lung for very long periods of time resulting in continuous damage, even if the patient is removed from the exposure. Because of this long latency period (often up to 30-50 years), individuals exposed in the past remain at increased risk of MM and other cancers throughout their lives.

Chemoprevention of cancer aims to prevent, arrest, or reverse either the initiation phase of carcinogenesis or the progression of neoplastic cells to cancer. Although this definition sounds simple, it has been very difficult to find effective chemopreventive agents. First, the mechanisms by which carcinogens induce cancer usually involve multiple mechanisms, making efficacy challenging and requiring an agent with multiple activities. Second, since the agent will be used to prevent a small number of tumors in a large population of healthy, but at-risk individuals, it must be extraordinarily non-toxic, well-tolerated, and affordable.

It is, therefore, also of high importance to identify agents (i.e., chemopreventive agents) that can be administered before, during, and exposure to carcinogens or other harmful chemical agents, such as chemical warfare agents, chlorine and hypochlorite ions and other harmful toxicants.

SUMMARY OF THE INVENTION

In one aspect, the invention provides a method for treating asthma in a subject in need thereof, the method comprising: administering to the subject a therapeutically effective amount of chemically synthesized secoisolaricirecinol diglucoside (SDG).

In another aspect, the invention provides a method for treating ozone-induced damage in a biomolecule, a cell, or a tissue of a subject in need thereof, the method comprising: administering to the subject a therapeutically effective amount of chemically synthesized SDG, wherein the biomolecule, the cell, or the tissue is located in a respiratory airway of the subject.

In a further aspect, the invention provides a method for protecting a biomolecule, a cell, or a tissue from ozone-induced damage in a subject in need thereof, the method comprising: administering to the subject therapeutically effective amount of at least one bioactive ingredient, wherein the bioactive ingredient comprises a therapeutically effective amount of chemically synthesized SDG.

In one aspect, the invention provides a method for treating or preventing ozone-induced damage in a subject who has been or will be exposed to a dose of ozone, the method comprising: administering to the subject a therapeutically effective amount of chemically synthesized SDG.

Administration to said subjects encompasses administration prior to, during and after exposure to damaging ozone exposure. The time prior, during and post could be seconds, minutes, hours, days, weeks, months or even years. The bioactive ingredient encompasses secoisolaricirecinol diglucoside (SDG), in particular a racemic mixture of the SDG, analogs thereof, stereoisomers thereof, or a combination thereof.

In another aspect, the invention relates to a method for treating or preventing radiation damage in a subject who has been or will be exposed to radiation, the method comprising: administering to said subject an effective amount of at least one bioactive ingredient, wherein said bioactive ingredient comprises secoisolaricirecinol diglucoside (SDG), secoisolariciresinol (SECO), enterodiol (ED), enterolactone (EL), analogs thereof, stereoisomers thereof, or a combination thereof.

In another aspect, the invention relates to a method for protecting biomolecule (such as genetic material like a nucleic acid, a protein or a lipid), a cell, or a tissue, from radiation damage resulting from accidental radiation exposure in a subject in need thereof, the method comprising: administering to said subject an effective amount of flaxseed, its bioactive ingredient, degradant or a metabolite thereof.

In another aspect, the invention relates to a method for protecting biomolecule (such as genetic material like a nucleic acid, a protein or a lipid), a cell, or a tissue, from radiation damage resulting in aging.

In another aspect, the invention relates to a method for protecting a biomolecule (such as genetic material like a nucleic acid, a protein or a lipid), a cell, or a tissue from damage resulting from exposure to chemical carcinogens and toxicants both natural and synthetic.

In another aspect, the invention relates to a method for protecting a biomolecule (such as genetic material like a nucleic acid, a protein or a lipid), a cell, or a tissue, from radiation damage resulting from radiation therapy for cancer treatment in a subject in need thereof, the method comprising: administering to said subject an effective amount of flaxseed, its bioactive ingredient, degradant or a metabolite thereof.

In another aspect, the invention relates to a method for protecting a biomolecule (such as genetic material like a nucleic acid, a protein or a lipid), a cell, or a tissue from radiation damage in a subject in need thereof, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof. In some embodiments, the radiation damage results from accidental radiation exposure. In some embodiments, the radiation damage results from radiation therapy for cancer (e.g., lung cancer) treatment.

In another aspect, the invention relates to a method for preventing radiation induced damage to a biomolecule (such as genetic material like a nucleic acid, a protein or a lipid), a cell, or a tissue, in a subject in need thereof, the method comprising: administering to said subject an effective amount of flaxseed, its bioactive ingredient, or a metabolite thereof.

In another aspect, the invention relates to a method for preventing radiation induced damage to a biomolecule (such as genetic material like a nucleic acid, a protein or a lipid), a cell, or a tissue, in a subject in need thereof, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule (such as genetic material like a nucleic acid, a protein or a lipid), a cell, or a tissue, from radiation damage in a cell, the method comprising contacting said cell with an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule (such as genetic material like a nucleic acid, a protein or a lipid), a cell, or a tissue, from carcinogen damage in a subject in need thereof, the method comprising: administering to said subject an effective amount of flaxseed, its bioactive ingredient, degradant or a metabolite thereof. Administration to said subjects encompasses administration prior to, during and after exposure to damaging exposure to chemical carcinogens and toxicants both natural and synthetic. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule, from carcinogen damage resulting from accidental exposure to chemical carcinogens and toxicants both natural and synthetic in a subject in need thereof, the method comprising: administering to said subject an effective amount of flaxseed, its bioactive ingredient, degradant or a metabolite thereof.

In another aspect, the invention relates to a method for protecting a biomolecule (such as genetic material like a nucleic acid, a protein or a lipid), a cell, or a tissue, from damage from chemical carcinogens and toxicants both natural and synthetic resulting in lung cancer or mesothelioma.

In another aspect, the invention relates to a method for protecting a biomolecule (such as genetic material like a nucleic acid, a protein or a lipid), a cell, or a tissue, from carcinogen damage, the method comprising: contacting said biomolecule, cell, or tissue with an effective amount of a bioactive ingredient. Contact with said biomolecule, cell, or tissue encompasses contact prior to, during and after exposure to damaging exposure to chemical carcinogens and toxicants both natural and synthetic. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for treating or preventing carcinogen-induced damage, malignant transformation or cancer development in subject who has been or will be exposed to one or more carcinogens from carcinogen-induced cancer, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a subject exposed to one or more carcinogens from a carcinogen-induced cancer, the method comprising: administering to said subject an effective amount of flaxseed, its bioactive ingredient, or a metabolite thereof.

In another aspect, the invention relates to a method for protecting a biomolecule (such as genetic material like a nucleic acid, a protein or a lipid), a cell, or a tissue, from damage by hypochlorite ions in a subject in need thereof, the method comprising: administering to said subject an effective amount of flaxseed, its bioactive ingredient, degradant or a metabolite thereof. Administration to said subjects encompasses administration prior to, during and after exposure to damaging exposure to chemical carcinogens and toxicants both natural and synthetic. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for treating or preventing hypochlorite ion-induced damage in a subject who has been or will be exposed to hypochlorite ions, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule (such as genetic material like a nucleic acid, a protein or a lipid), a cell, or a tissue, from damage by hypochlorite ions, the method comprising: contacting said biomolecule, cell, or tissue exposed to or to be exposed to hypochlorite ions with an effective amount of a bioactive ingredient. Contact with said biomolecule, cell, or tissue encompasses contact prior to, during and after exposure to damaging exposure to chemical carcinogens and toxicants both natural and synthetic. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a composition for use in one of the foregoing methods.

Unless otherwise defined, all technical and scientific terms used herein have the same meaning as commonly understood by one of ordinary skill in the art to which this invention belongs. Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description. It is also contemplated that whenever appropriate, any embodiment of the present invention can be combined with one or more other embodiments of the present invention, even though the embodiments are described under different aspects of the present invention.

BRIEF DESCRIPTION OF THE DRAWINGS

FIG. 2A graphically depicts the measured total lung resistance in response to aerosolized methacholine into the lung; it was determined that at 1, 4, and 32 mg/mL, there was significant increase in lung resistance on day 8 compared to day 1 in placebo+$O_3$ animals, however there were no significant differences noted between day 1 and day 8 at any dose of methacholine for LGM2605+air or LGM2605+$O_3$ animals. FIG. 2B shows a plot of the percent change post treatment/exposure of methacholine EC150 that was calculated on day 1 and day 8; wherein day 1 is represented as 100%. FIG. 2C shows dose response curves to methacholine that were normalized, where each animal served as its own controls, thus day 1 is represented as 100%. FIG. 2D shows lung brushing gene expression of receptors involved in AHR that were studied in airway epithelial cells.

FIG. 3A shows total BAL cells quantification. FIG. 3B shows total BAL cells that were normalized to day 1 measurements. FIG. 3C shows representative KwikDiff stained cytospins. FIG. 3D shows BAL macrophages, lymphocytes, neutrophils, and eosinophils that were quantified by differential cell count.

FIG. 5A shows representative flow plots, gated from the BAL ILC population (liveCD90+Lineage−CD127+ cells). ILC2s were defined as CD25+ckit(var) ILCs. FIG. 5B shows the absolute number of BAL ILC2s that was calculated. FIG. 5C shows the relative distribution of ILC family members displayed via part of whole charts.

FIG. 6A shows isolated ILC2 gene expression; 70 ng RNA reverse transcribed from blood Lin−CD90+CD25+ckit(var) cells (ILC2s). log($\Delta\Delta Ct$) values were calculated first to GAPDH, then to day 1. FIG. 6B shows that $\Delta\Delta Ct$ values were correlated to BAL neutrophilia in placebo+$O_3$.

FIG. 7A shows representative flow plots of CD1c+ mDCs, gated live CD45+CD11c+HLA−DR+ cells. FIG. 7B shows representative flow plots of CD16+ mDC s, gated live CD45+CD11c+HLA−DR+ cells. FIG. 7C shows representative flow plots of CD123+ pDC s, gated live CD45+CD11c−HLA−DR+ cells. FIG. 7D shows relative distribution of DC subsets displayed via part of whole charts. FIG. 7E shows the absolute number of BAL DCs that was calculated. FIG. 7F shows that LGM2605 treatment alone caused a significant reduction in the number of CD1c+mDCs and CD16+ mDCs in the BAL (graphed as a % change of absolute BAL cells (Day8/Day1).

FIG. 8A shows representative flow plots defining CD4+CD8− and CD4−CD8+ T cells in the BAL. Cells were gated initially as live CD45+CD3+ cells. FIGS. 8B-8C show the absolute number of BAL CD8+ and CD4+ T cells that was calculated. FIG. 8D shows the relative distribution of CD4+ and CD8+ T cells displayed via part of whole charts. FIG. 8E shows BAL CD4+ T cell activation that was measured by gating on CD25+ cells.

FIGS. 9A-9B show BAL total protein that was quantified via BCA Assay and percent change was determined form day 1 to day 8. FIGS. 9C-9D show representative reducing and native-PAGE western blots to detect BAL SP-D. Mouse recombinant SP-D was used as a loading control. FIGS. 9E-9F show the semi-quantitative densitometry that was performed on reducing and native-PAGE gels via ImageJ to determine the percent change in total and de-oligomerized BAL SP-D. FIGS. 9G-9H show the percent change in total and de-oligomerized SP-D was correlated to AHR, BAL neutrophilia, and BAL eosinophilia.

FIG. 12A shows representative flow plots, gated from the blood ILC population (liveCD90+Lineage−CD127+ cells). ILC2s were defined as CD25+ckit(var) ILCs. FIG. 12B shows the absolute number of blood ILC2s was calculated after treatment and exposure. FIG. 12C shows the relative distribution of ILC family members displayed via part of whole charts.

FIG. 14A shows representative flow plots of CD1c+ mDC s, gated live CD45+CD11c+HLA−DR+ cells. FIG. 14B shows representative flow plots of CD16+mDCs, gated live CD45+CD11c+HLA−DR+ cells. FIG. 14C shows representative flow plots of CD123+ pDC s, gated live CD45+CD11c−HLA−DR+ cells. FIG. 14D shows the absolute number of blood DCs was calculated.

FIG. 16A shows representative flow plots defining CD4+CD8− and CD4−CD8+ T cells in the blood. Cells were gated initially as live CD45+CD3+ cells. FIGS. 16B-16C show the absolute number of blood CD8+ and CD4+ T cells that was calculated. FIG. 16D shows blood CD4+ T cell activation that was measured by gating on CD25+ cells.

DETAILED DESCRIPTION OF THE INVENTION

Figure 1:
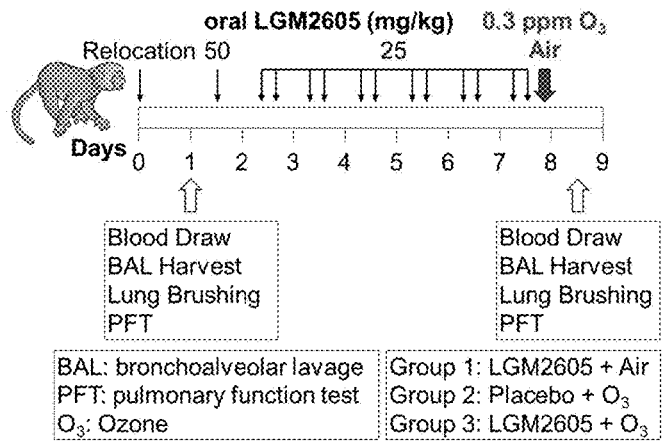
FIG. 1 illustrates the study design and experimental groups in accordance with embodiments described herein, in particular whether ozone exposure caused pulmonary inflammation and AHR in rhesus macaques and whether oral treatment of chemically synthesized SDG (also called "LG2605" herein) for 7 days could dampen the inflammation or AHR induced by ozone inhalation.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Provided herein are therapeutic and prophylactics methods of using flaxseed, its bioactive ingredients, or its metabolites for radioprotection and chemoprevention. In exemplary embodiments, the bioactive ingredient comprises the chemically synthesized secoisolariciresinol diglucoside (SDG), and in particular, a racemic mixture of the SDG, analogs thereof, isomers (including stereoisomers) thereof, or a combination thereof. SDG, which is a precursor of mammal lignans, its analogs include secoisolariciresinol (SECO), which is formed from SDG, and mammalian ligans (enterolignans), such as enterodiol (ED) and enterolactone (EL).

The inventors of this application have found that flaxseed, its bioactive ingredients, and/or its degradants or metabolites are effective in protecting biomolecules, cells, and tissues from ozone damage, radiation damage, hypochlorite ion-induced damage, carcinogen-induced damage and malignancy. Accordingly, the inventors have found that flaxseed, its bioactive ingredients, or its metabolites can be used for protecting biomolecules, cells, and tissues from ozone damage, radiation damage, hypochlorite ion-induced damage, carcinogen damage and cancer development.

In one aspect, the invention provides a method for treating asthma in a subject in need thereof, the method comprising: administering to the subject a therapeutically effective amount of chemically synthesized secoisolariciresinol diglucoside (SDG).

In an embodiment, the chemically synthesized SDG comprises a racemic mixture of the SDG. In some embodiments, the chemically synthesized SDG comprises (S,S)-SDG or (R,R)-SDG or a combination of (S,S)-SDG and (R,R)-SDG, including a racemic mixture of (S,S)-SDG and (R,R)-SDG. In particular embodiments, the asthma is a steroid-resistant asthma. In some embodiments, the administration of the chemically synthesized SDG alleviates or eliminates respiratory airway hyperactivity in the subject. In an embodiment, the respiratory airway is an upper respiratory airway, a lower respiratory airway or a combination thereof. In another embodiment, the administration of the chemically synthesized SDG alleviates or eliminates bronchoalveolar lavage (BAL) inflammation in the subject. In some embodiments, alleviation or elimination of the BAL inflammation comprises reducing BAL neutrophilia. In an embodiment, the administration of the chemically synthesized SDG alleviates or eliminates oxidative stress. In certain embodiments, the chemically synthesized SDG inhibits surfactant protein-D (SP-D) de-oligomerization. In various embodiments, the subject is a human subject. In some embodiments, the chemically synthesized SDG is administered in a dietary composition. In particular embodiments, the chemically synthesized SDG is administered orally. In some embodiments, the chemically synthesized SDG is in a concentration about 1 nanomolar (nM) to about 1 molar (M). In further embodiments, the SDG concentration is about 25 µM to about 250 µM. In particular embodiments, the subject is a human subject.

In another aspect, the invention provides a method for treating ozone-induced damage in a biomolecule, a cell, or a tissue of a subject in need thereof, the method comprising: administering to the subject a therapeutically effective amount of chemically synthesized SDG, wherein the biomolecule, the cell, or the tissue is located in a respiratory airway of the subject.

In an embodiment, the chemically synthesized SDG comprises a racemic mixture of the SDG. In various embodiments, the chemically synthesized SDG comprises (S,S)-SDG or (R,R)-SDG or a combination of (S,S)-SDG and (R,R)-SDG, including a racemic mixture of (S,S)-SDG and (R,R)-SDG. In some embodiments, administration of the chemically synthesized SDG alleviates or eliminates respiratory airway hyperactivity in the subject. In various embodiments, the respiratory airway is an upper respiratory airway, a lower respiratory airway or a combination thereof. In some embodiments, administration of the chemically synthesized SDG alleviates or eliminates BAL inflammation in the subject. In certain embodiments, alleviation or elimination of the BAL inflammation comprises reducing ozone-induced BAL neutrophilia. In some embodiments, administration of the chemically synthesized SDG alleviates or eliminates oxidative stress. In various embodiments, the chemically synthesized SDG inhibits surfactant protein-D (SP-D) de-oligomerization. In particular embodiments, the chemically synthesized SDG protects the biomolecule, the cell, or the tissue from ozone-induced IL-6, IL-25, IL-33, and CCL11 gene expression in respiratory airway epithelial cells. In an embodiment, the chemically synthesized SDG reduces BAL group 2 innate lymphoid cells (ILC2) and CD1c+ mDC dendritic cells in the respiratory airway of the subject. In some embodiments, the subject is one who will be exposed to ozone. In further embodiments, the subject is one who has been exposed to ozone. In particular embodiments, the subject is a human subject. In some embodiments, the chemically synthesized SDG is administered in a dietary composition. In certain embodiments, the chemically synthesized SDG is administered orally. In some embodiments, the chemically synthesized SDG is in a concentration about 1 nanomolar (nM) to about 1 molar (M). In further embodiments, the SDG concentration is about 25 µM to about 250 µM. In particular embodiments, the subject is a human subject.

In a further aspect, the invention provides a method for protecting a biomolecule, a cell, or a tissue from ozone-induced damage in a subject in need thereof, the method comprising: administering to the subject therapeutically effective amount of at least one bioactive ingredient, wherein the bioactive ingredient comprises a therapeutically effective amount of chemically synthesized SDG. In some embodiments, the chemically synthesized SDG comprises a racemic mixture of the SDG. In various embodiments, the chemically synthesized SDG comprises (S,S)-SDG or (R,R)-SDG or a combination of (S,S)-SDG and (R,R)-SDG, including a racemic mixture of (S,S)-SDG and (R,R)-SDG. In an embodiment, the biomolecule is a nucleic acid. In another embodiment, the biomolecule is a protein or a lipid. In some embodiments, the chemically synthesized SDG is an SDG analog. In particular embodiments, the chemically synthesized SDG is administered in a dietary composition. In some embodiments, said step of administering comprises orally administering. In certain embodiments, the chemically synthesized SDG is in a concentration about 1 nanomolar (nM) to about 1 molar (M). In further embodiments, the SDG concentration is about 25 µM to about 250 µM. In particular embodiments, the subject is a human subject.

In one aspect, the invention provides a method for treating or preventing ozone-induced damage in a subject who has been or will be exposed to a dose of ozone, the method comprising: administering to the subject a therapeutically effective amount of chemically synthesized SDG. In an embodiment, the chemically synthesized SDG comprises a racemic mixture of the SDG. In another embodiment, the chemically synthesized SDG comprises (S,S)-SDG or (R,R)-SDG or a combination of (S,S)-SDG and (R,R)-SDG, including a racemic mixture of (S,S)-SDG and (R,R)-SDG. In a further embodiment, administration of the chemically synthesized SDG alleviates or eliminates respiratory airway hyperactivity in the subject. In some embodiments, the ozone-induced damage is a respiratory airway hyperactivity, a respiratory airway inflammation, oxidative stress of a respiratory airway or a combination thereof. In certain embodiments, the respiratory airway is an upper respiratory airway, a lower respiratory airway or a combination thereof. In some embodiments, administration of the chemically synthesized SDG alleviates or eliminates bronchoalveolar lavage (BAL) inflammation in the subject. In various embodiments, wherein alleviation or elimination of the BAL inflammation comprises reducing BAL neutrophilia. In an embodiment, the oxidative stress causes de-oligomerization of surfactant protein-D (SP-D). In some embodiments, administration of the chemically synthesized SDG alleviates or eliminates oxidative stress. In an embodiment, the chemically synthesized SDG inhibits surfactant protein-D (SP-D) de-oligomerization. In some embodiments, the chemically synthesized SDG is administered in a dietary composition. In various embodiments, the chemically synthesized SDG is administered orally. In particular embodiments, the chemically synthesized SDG is in a concentration about 1 nanomolar (nM) to about 1 molar (M). In some embodiments, wherein the SDG concentration is about 25 µM to about 250 µM. In particular embodiments, the subject is a human subject.

Subjects in need of ozone-damage protection, radioprotection or radiation mitigation according to methods provided herein are subjects who will, are, or have been exposed to potentially deleterious amounts of ozone, or in other embodiments to deleterious amounts of radiation. It will be understood that such exposure may be a single exposure, periodic exposure, sporadic exposure or ongoing exposure to the ozone (or in other embodiments to radiation). It is also understood that such ozone exposure includes accidental exposure, incidental or intentional exposure; likewise, radiation exposure includes accidental exposure, incidental or intentional exposure.

Examples of subjects who may be in need of protection from ozone exposure or subsequent to ozone exposure, include populations residing in areas where ozone levels are elevated for prolonged periods. Additional examples of subjects in need of protection from ozone exposure or subsequent to ozone exposure, include subjects residing in rural areas, where emissions of nitrogen oxides are responsible for much of the ozone formation. In further embodiments, subjects in need of protection from ozone exposure or subsequent to ozone exposure, include human and animal subject exposed to ozone at or close to ambient concentrations of ozone or exposed to episodes of increased ozone, which occurs during the summer, the episodes usually occurring under anticyclonic conditions coinciding with increased sunlight, high temperatures and low wind speed, e.g., in polluted urban areas and in rural regions. Additional examples of subjects in need of protection from ozone exposure or subsequent to ozone exposure, include subjects who have been accidentally exposed to environmental or elevated ozone, including but not limited to in a laboratory or industrial facility.

Examples of subjects who may be in need of radioprotection or radiation mitigation according to the methods of the present invention include but are not limited to, patients who are exposed to radiation as part of therapeutic regimen (e.g., cancer patients who require radiation therapy), subjects who are exposed to radiation for to diagnose a disease or condition (e.g., subjects receiving dental or bone X-rays, patients receiving PET scans, CT scans and the like). Examples of subjects who may be in need of radioprotection or radiation mitigation according to the methods of the present invention also include those who may be exposed to radiation as a result of their profession or life style choices (e.g., airplane flight crews or other frequent air travelers, and even space travelers, who are exposed to higher than average radiation levels; laboratory technicians and other workers; or those exposed through the use of electronic devices) or those exposed to accumulations of radon (e.g., accumulations in dwellings or mines) or outdoor workers or sunbathers exposed to natural radiation from the sun. Other subjects who may be in need of radioprotection according to the methods of the present invention include those who are accidentally exposed to radiation, such as leaks or spills, (e.g., nuclear reactor leaks or accidents or laboratory spills). Also contemplated are those exposed to radiation as a result of the detonation of a nuclear warhead, as a result of war or terrorism. Additional subjects encompassed are those who are exposed to a terrorist's detonation of conventional explosives that disperse radioactive materials.

Subjects in need of chemoprevention according to methods provided herein are subjects who will, are, or have been exposed to potentially deleterious amounts of carcinogens or other toxicants. It will be understood that such exposure may be a single exposure, periodic exposure, sporadic exposure or ongoing exposure to one or combination of several synthetic or naturally occurring carcinogens or other toxicants, such as chemical warfare agents. It is also understood that such exposure includes accidental exposure, incidental or intentional exposure. It will also be understood that such exposure may be direct exposure or indirect exposure. For example, indirect exposure to hypochlorite ions may be the result of direct exposure to ionizing radiation.

Examples of subjects who may be in need of chemoprevention according to the methods of the present invention include but are not limited to those who may be exposed to carcinogens or other toxicants as a result of their profession or life style choices (e.g., workers in the oil industry; toll booth attendants exposed to automobile exhaust particles; laboratory technicians and other workers). Other subjects who may be in need of chemoprevention according to the methods of the present invention include those who are accidentally exposed to carcinogens, such as leaks or spills of carcinogens in the drinking water or the air (asbestos, polyaromatic hydrocarbons). Also contemplated are those exposed to carcinogens as a result of a habit (smokers). Additional subjects encompassed are those who are exposed to a terrorist's act to disperse carcinogen and other cancer promoting materials, such as chemical warfare agents.

In one aspect, the invention relates to a method for protecting a biomolecule (such as genetic material like a nucleic acid, a protein or a lipid), a cell, or a tissue, from radiation damage in a subject in need thereof, the method comprising: administering to said subject an effective amount of flaxseed, its bioactive ingredient, degradant or a metabolite thereof. Administration to said subjects encompasses administration prior to, during and after exposure to damaging radiation exposure. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for treating or preventing radiation damage in a subject who has been or will be exposed to radiation, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting biomolecule (such as genetic material like a nucleic acid, a protein or a lipid), a cell, or a tissue, from radiation damage resulting from accidental radiation exposure in a subject in need thereof, the method comprising: administering to said subject an effective amount of flaxseed, its bioactive ingredient, degradant or a metabolite thereof.

In another aspect, the invention relates to a method for protecting biomolecule (such as genetic material like a nucleic acid, a protein or a lipid), a cell, or a tissue, from radiation damage resulting in aging.

In another aspect, the invention relates to a method for protecting a biomolecule (such as genetic material like a nucleic acid, a protein or a lipid), a cell, or a tissue from damage resulting from exposure to chemical carcinogens and toxicants, including chemical warfare agents, both natural and synthetic.

In another aspect, the invention relates to a method for protecting a biomolecule (such as genetic material like a nucleic acid, a protein or a lipid), a cell, or a tissue, from radiation damage resulting from radiation therapy for cancer treatment in a subject in need thereof, the method comprising: administering to said subject an effective amount of flaxseed, its bioactive ingredient, degradant or a metabolite thereof.

In another aspect, the invention relates to a method for protecting a biomolecule (such as genetic material like a nucleic acid, a protein or a lipid), a cell, or a tissue from radiation damage in a subject in need thereof, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof. In some embodiments, the radiation damage results from accidental radiation exposure. In some embodiments, the radiation damage results from radiation therapy for cancer (e.g., lung cancer) treatment.

In another aspect, the invention relates to a method for preventing radiation induced damage to a biomolecule (such as genetic material like a nucleic acid, a protein or a lipid), a cell, or a tissue, in a subject in need thereof, the method comprising: administering to said subject an effective amount of flaxseed, its bioactive ingredient, or a metabolite thereof.

In another aspect, the invention relates to a method for preventing radiation induced damage to a biomolecule (such as genetic material like a nucleic acid, a protein or a lipid), a cell, or a tissue, in a subject in need thereof, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule (such as genetic material like a nucleic acid, a protein or a lipid), a cell, or a tissue, from radiation damage in a cell, the method comprising contacting said cell with an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule (such as genetic material like a nucleic acid, a protein or a lipid), a cell, or a tissue, from carcinogen damage in a subject in need thereof, the method comprising: administering to said subject an effective amount of flaxseed, its bioactive ingredient, degradant or a metabolite thereof. Administration to said subjects encompasses administration prior to, during and after exposure to damaging exposure to chemical carcinogens and toxicants both natural and synthetic. The time prior, during and post could be seconds, minutes, hours, days, weeks, months or even years. The bioactive ingredient encompasses secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule, from carcinogen damage resulting from accidental exposure to chemical carcinogens and toxicants both natural and synthetic in a subject in need thereof, the method comprising: administering to said subject an effective amount of flaxseed, its bioactive ingredient, degradant or a metabolite thereof.

In another aspect, the invention relates to a method for protecting a biomolecule (such as genetic material like a nucleic acid, a protein or a lipid), a cell, or a tissue, from damage from chemical carcinogens and toxicants both natural and synthetic resulting in lung cancer or mesothelioma.

In another aspect, the invention relates to a method for protecting a biomolecule (such as genetic material like a nucleic acid, a protein or a lipid), a cell, or a tissue, from carcinogen damage, the method comprising: contacting said biomolecule, cell, or tissue with an effective amount of a bioactive ingredient. Contact with said biomolecule, cell, or tissue encompasses contact prior to, during and after exposure to damaging exposure to chemical carcinogens and toxicants both natural and synthetic. The time prior, during and post could be seconds, minutes, hours, days, weeks, months or even years. The bioactive ingredient encompasses secoisolaricirecinol diglucoside (SDG), secoisolariciresinol (SECO), enterodiol (ED), enterolactone (EL), analogs thereof, stereoisomers thereof, or a combination thereof.

In another aspect, the invention relates to a method for treating or preventing carcinogen-induced damage, malignant transformation or cancer development in subject who has been or will be exposed to one or more carcinogens from carcinogen-induced cancer, the method comprising: administering to said subject an effective amount of at least one bioactive ingredient, wherein said bioactive ingredient comprises secoisolaricirecinol diglucoside (SDG), secoisolariciresinol (SECO), enterodiol (ED), enterolactone (EL), analogs thereof, stereoisomers thereof, or a combination thereof.

In another aspect, the invention relates to a method for protecting a subject exposed to one or more carcinogens from a carcinogen-induced cancer, the method comprising: administering to said subject an effective amount of flaxseed, its bioactive ingredient, or a metabolite thereof.

In another aspect, the invention relates to a method for protecting a biomolecule (such as genetic material like a nucleic acid, a protein or a lipid), a cell, or a tissue, from damage by hypochlorite ions in a subject in need thereof, the method comprising: administering to said subject an effective amount of flaxseed, its bioactive ingredient, degradant or a metabolite thereof. Administration to said subjects encompasses administration prior to, during and after exposure to damaging exposure to chemical carcinogens and toxicants both natural and synthetic. The time prior, during and post could be seconds, minutes, hours, days, weeks, months or even years. The bioactive ingredient encompasses secoisolaricirecinol diglucoside (SDG), secoisolariciresinol (SECO), enterodiol (ED), enterolactone (EL), analogs thereof, stereoisomers thereof, or a combination thereof.

In another aspect, the invention relates to a method for treating or preventing hypochlorite ion-induced damage in a subject who has been or will be exposed to hypochlorite ions, the method comprising: administering to said subject an effective amount of at least one bioactive ingredient, wherein said bioactive ingredient comprises secoisolariciresinol diglucoside (SDG), secoisolariciresinol (SECO), enterodiol (ED), enterolactone (EL), analogs thereof, stereoisomers thereof, or a combination thereof.

In another aspect, the invention relates to a method for protecting a biomolecule (such as genetic material like a nucleic acid, a protein or a lipid), a cell, or a tissue, from damage by hypochlorite ions, the method comprising: contacting said biomolecule, cell, or tissue exposed to or to be exposed to hypochlorite ions with an effective amount of a bioactive ingredient. Contact with said biomolecule, cell, or tissue encompasses contact prior to, during and after exposure to damaging exposure to chemical carcinogens and toxicants both natural and synthetic. The time prior, during and post could be seconds, minutes, hours, days, weeks, months or even years. The bioactive ingredient encompasses secoisolaricirecinol diglucoside (SDG), secoisolariciresinol (SECO), enterodiol (ED), enterolactone (EL), analogs thereof, stereoisomers thereof, or a combination thereof.

In another aspect, the invention relates to a composition for use in one of the foregoing methods.

Flaxseed, its bioactive ingredients, and its metabolites are known in the art and described in U.S. Patent Publication Nos. 2010/0239696; 2011/0300247; and 2014/0308379; and in International Patent Publication No. WO2014/200,964, each of which is incorporated by reference herein in its entirety.

The primary lignan found in flaxseed is 2,3-bis(3-methoxy-4-hydroxybenzyl) butane-1,4-diol (secoisolariciresinol or SECO), which is stored as the conjugate secoisolariciresinol diglucoside (SDG) in its native state in the plant. SDG is metabolized in the human intestine to enterodiol (ED), and enterolactone (EL). Synthetic analogs of enterodiol and enterolactone are known (see, e.g., Eklund et al., *Org. Lett.*, 2003, 5:491).

A "degradant" is a product of the breakdown of a molecule, such as SDG, into smaller molecules.

A "metabolite" is a substance produced by metabolism or by a metabolic process. For example, a metabolite of SDG is EL or ED.

It will be appreciated by one skilled in the art that a metabolite may be a chemically synthesized equivalent of a natural metabolite.

An "analog" is a compound whose structure is related to that of another compound. The analog may be a synthetic analog.

An "ingredient" or "component" is an element or a constituent in a mixture or compound.

A "product" is a substance resulting from a chemical reaction.

An "extract" is a preparation containing an active principle or concentrated essence of a material, for example, from flaxseed.

"Pharmaceutical composition" refers to an effective amount of an active ingredient, e.g., (S,S)-SDG (R,R)-SDG, meso-SDG, SDG, SECO, EL, ED and analogs thereof, together with a pharmaceutically acceptable carrier or diluent. A "therapeutically effective amount" refers to that amount which provides a therapeutic effect for a given condition and administration regimen.

The compositions described herein may include a "therapeutically effective amount." A "therapeutically effective amount" refers to an amount effective, at dosages and for periods of time necessary, to achieve the desired therapeutic result. A therapeutically effective amount may vary according to factors such as the disease state, age, sex, and weight of the individual, and the ability of the composition to elicit a desired response in the individual. A therapeutically effective amount is also one in which toxic or detrimental effects of the molecule are outweighed by the therapeutically beneficial effects.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used herein includes both one and more than one such excipient.

The pharmaceutical compositions can be administered to a subject by any suitable method known to a person skilled in the art, such as orally, parenterally, transmucosally, transdermally, intramuscularly, intravenously, intra-dermally, subcutaneously, intra-peritonealy, intra-ventricularly, intra-cranially, intra-vaginally, intra-tumorally, or bucally. Controlled release may also be used by embedding the active ingredient in an appropriate polymer which may then be inserted subcutaneously, intratumorally, bucally, as a patch on the skin, or vaginally Coating a medical device with the active ingredient is also covered.

In some embodiments, the pharmaceutical compositions are administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like. In some embodiments, the active ingredient is formulated in a capsule. In accordance with this embodiment, the compositions of the present invention comprise, in addition to the active compound and the inert carrier or diluent, drying agent, in addition to other excipients as well as a gelatin capsule.

In some embodiments, the pharmaceutical compositions are administered by intravenous, intra-arterial, or intra-muscular injection of a liquid preparation. In some embodiments, the pharmaceutical composition is a liquid preparation formulated for oral administration. In some embodiments, the pharmaceutical composition is a liquid preparation formulated for intravaginal administration. Suitable liquid formulations include solutions, suspensions, dispersions, emulsions, oils and the like. In some embodiments, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In some embodiments, the pharmaceutical compositions are administered intra-muscularly and are thus formulated in a form suitable for intra-muscular administration. In some embodiments, the pharmaceutical compositions are administered intra-bucally and are thus formulated in a form suitable for buccal administration.

In some embodiments, the pharmaceutical compositions are administered topically to body surfaces and are thus formulated in a form suitable for topical administration. Suitable topical formulations include gels, ointments, creams, lotions, drops, controlled release polymers and the like. For topical administration, the flaxseed, its bioactive ingredient, or a metabolite thereof is prepared and applied as a solution, suspension, or emulsion in a physiologically acceptable diluent with or without a pharmaceutical carrier.

In some embodiments, the pharmaceutical compositions provided herein are controlled-release compositions, i.e. compositions in which the flaxseed, its bioactive ingredient, or a metabolite thereof is released over a period of time after administration. Controlled- or sustained-release compositions include formulation in lipophilic depots (e.g. fatty acids, waxes, oils). In other embodiments, the composition is an immediate-release composition, i.e. a composition in which all the flaxseed, its bioactive ingredient, or a metabolite thereof is released immediately after administration.

In some embodiments, compositions for use in the methods provided herein are administered at a therapeutic dose once per day. In some embodiments, the compositions are administered once every two days, twice a week, once a week, or once every two weeks.

Techniques for extracting and purifying SDG are known in the art and described in U.S. Pat. No. 5,705,618, which is incorporated herein by reference. Techniques for synthesizing SDG, its stereoisomers and analogs are described in Mishra O P, et al. *Bioorganic & Medicinal Chemistry Letters* 2013, (19):5325-5328 and in International Patent Publication No. WO2014/200,964, which are hereby incorporated by reference in their entireties. Bioactive components for use in the methods provided herein may also be chemically synthesized directly into the mammalian, readily metabolizable forms, Enterodiol (ED) or Enterolactone (EL), as is known in the art.

(S,S)-SDG (R,R)-SDG, (S,R)-SDG (R,S)-SDG, meso-SDG, SECO, EL, ED or an analog thereof may be administered at a dose of 0.1 ng/kg to 500 mg/kg.

The treatment with (S,S)-SDG (R,R)-SDG, (S,R)-SDG (R,S)-SDG, meso-SDG, SDG, SECO, EL, ED or an analog thereof is a single administration to several days, months, years, or indefinitely.

As used herein, "treating" may refer to either therapeutic treatment or prophylactic or preventative measures, wherein the object is to prevent or lessen the targeted pathologic condition or disorder as described herein, or both. Therefore, compositions for use in the methods provided herein may be administered to a subject before the exposure, e.g., to radiation, a carcinogen, a toxicant, or hypochlorite ions. In some cases, compositions for use in the methods provided herein may be administered to a subject after the exposure. Thus treating a condition as described herein may refer to preventing, inhibiting, or suppressing the condition in a subject.

Furthermore, as used herein, the terms "treat" and "treatment" refer to therapeutic treatment, as well prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment. Those in need of treatment include those already having been exposed, e.g., to radiation, a carcinogen, a toxicant, or hypochlorite ions, as well as those prone to being exposed or those expecting to be exposed.

In some embodiments, subjects in need of treatment and the methods and compositions described herein may include, but are not limited to, subjects with lung diseases and disorders, such as asthma, in particular steroid-resistant asthma, cancer, COPD, and mesothelioma. In some embodiments, suitable subjects may include subjects with disorders and conditions associated with aging, such as cardiovascular disorders and conditions, sagging skin and central nervous system (CNS) diseases (e.g., Alzheimer's dementia). In some embodiments, suitable subjects may include skin disorders and conditions (e.g., psoriasis), as well as subjects with cosmetic skin conditions (e.g., wrinkles and age spots). In some embodiments, suitable subjects may include subjects with gastrointestinal disorders and conditions, such as IBD and Crohn's disease. In some embodiments, suitable subjects may include subjects with cardiovascular disorders and conditions. In some embodiments, suitable subjects may include subjects with melanoma. In some embodiments, suitable subjects may include subjects with ocular diseases, such as macular degeneration. In some embodiments, suitable subjects may include subjects with cancer, such as breast cancer, prostate cancer and uterine cancer. In some embodiments, suitable subjects include subjects with cognitive impairment and other cognitive disorders.

The term "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In addition to humans, the subject may include dogs, cats, pigs, cows, sheep, goats, horses, buffalo, ostriches, guinea pigs, rats, mice, birds (e.g., parakeets) and other wild, domesticated or commercially useful animals (e.g., chicken, geese, turkeys, fish). The term "subject" does not exclude an individual that is normal in all respects. The term "subject" includes, but is not limited to, a human in need of therapy for, or susceptible to, a condition or its sequelae.

The term "about" or "approximately" means within an acceptable error range for the particular value as determined by one of ordinary skill in the art, which will depend in part on how the value is measured or determined, i.e., the limitations of the measurement system.

The following examples are presented in order to more fully illustrate the preferred embodiments of the invention. They should in no way be construed, however, as limiting the broad scope of the invention.

EXAMPLES

Compounds with antioxidant and free radical scavenging properties can function as ozone-damage protectors, as well as radioprotectors and prevent radiation-induced DNA damage. Due to complex extraction, purification and enrichment methods to isolate secoisolariciresinol diglucoside (SDG) from natural resources associated with high costs, variability and difficulty to produce large quantities of SDG to make preclinical and clinical testing feasible, SDG was chemically synthesized. Using the natural compounds vanillin and glucose, two enantiomers (their structures are depicted below) of SDG: SDG (S,S) and SDG (R,R), were successfully synthesized (Mishra et al., *Bioorganic & Medicinal Chemistry Letters* 2013, (19):5325).

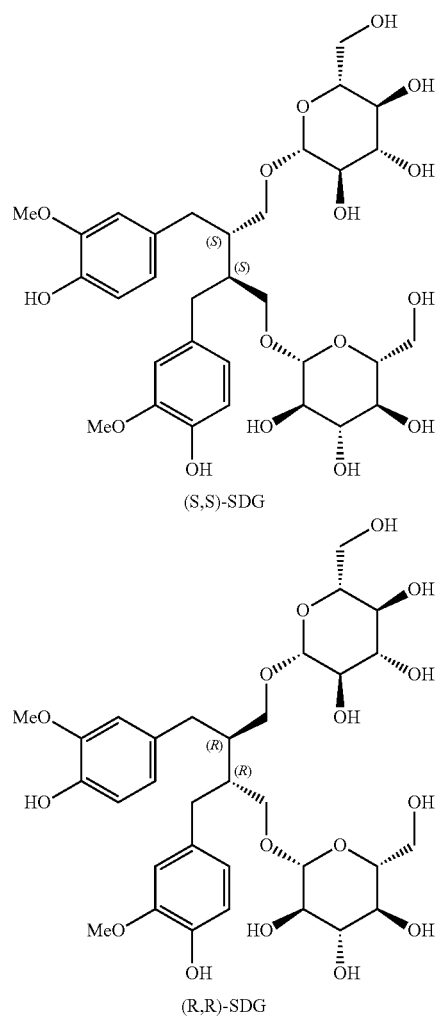

SDG has been shown in many studies by Christofidou-Solomidou et al., in addition to others, to be a potent antioxidant agent and a potent free radical scavenger. Importantly, in a recent study, the synthetic SDG enantiomers have been shown to possess strong antioxidant and free radical, scavenging characteristics (Mishra et al., *Bioorganic & Medicinal Chemistry Letters* 2013, (19):5325-5328). The radioprotective properties of the synthesized SDG enantiomers (S,S)-SDG and (R,R)-SDG as they compare to the commercial SDG were investigated and evaluated, as described in U.S. patent application Ser. No. 15/315,349, filed Nov. 30, 2016, which is incorporated by reference in its entirety. SDG is metabolized by intestinal bacteria to produce secoisolariciresinol (SECO), enterodiol (ED) and enterolactone (EL). Therefore, the effect of these metabolites of SDG on γ-irradiation-induced fragmentation of genomic DNA has also been evaluated as described in U.S. patent application Ser. No. 15/315,349, filed Nov. 30, 2016. which is incorporated by reference in its entirety.

Example 1

$O_3$ causes oxidative stress, airway inflammation and AHR. LGM2605 is an anti-inflammatory and anti-oxidant compound. It was hypothesized that LGM2605 treatment alleviates airway inflammation and AHR caused by $O_3$ inhalation in rhesus macaques. The aim of the studies was to investigate the effects of LGM2605 on peripheral blood and BAL immune cells [innate lymphoid cells (ILCs), dendritic cells (DCs) and T cells] and to evaluate expression of anti-oxidant genes, cytokines, and surfactant proteins in airway epithelial brushings and BAL. This study was conducted in a carefully selected cohort on asthmatic rhesus monkeys, a principal animal model for studies of human asthma.

Materials and Methods

Synthesis of Secoisolariciresinol Diglucoside (SDG)

Synthetic SDG (R,R) and SDG (S,S) stereoisomers may be synthesized as described in Mishra et al., *Bioorganic & Medicinal Chemistry Letters* 2013, (19):5325-5328.

LGM2605 Formulation

LGM2605 was supplied by Lignamed LLC. LGM2605 was procured from Wilmington PharmaTech. Chemical purity was determined to be 97.5%, as shown in a Certificate of Analysis. It was received lyophilized and prepared at 0.62 mg/mL in sterile water and stored at −80° C. in 1 mL aliqouts. One aliquot was thawed at a time, and stored at 4° C. until it was completely used for the study.

Ozone Exposure $O_3$ exposures were conducted in 4.2 cubic meter stainless steel and glass, whole-body inhalation chambers. $O_3$ was produced from a vaporized liquid, medical grade oxygen by electric discharge ozonizers. $O_3$ was mixed with filtered dilution air and injected into the inlet air-flow of the exposure chamber with 30 air changes per hour. $O_3$ concentration, airflow, temperature, pressure, and humidity were monitored throughout the exposure. Filtered air was injected into the inlet air-flow of the exposure chamber with 30 changes per hour for the LGM2605+ air experimental group.

Subjects

Non-human primate (NHP) rhesus macaques were acquired from the California National Primate Research Center (CNPRC) breeding colony at the University of California, Davis. Monkeys were identified via their unique number tattoo. Diet consisted of Purina Monkey Chow, 25% protein, pre-analyzed. There were no known contaminants in this feed which could interfere with the conduct of the study. Fruit and other supplements were given according to CNPRC Psychological well-being plan. Drinking water was provided ad libitum by automatic lixit devices. General mineral analyses, inorganic chemical analyses, electrical conductivity, and bacteriological screens were performed at regular intervals per CNPRC Standard Operating Procedures (SOP) #KK-4. Male and female NHPs were recruited to the study as 2-3 year olds and relocated from their native outdoor field cages to experimental rooms. Once indoors, animals were individually housed in stainless steel Harford hanging cages (4.2 square feet). All housing was in compliance with established standards of the Federal Animal Welfare Act and the Institute for Laboratory Animal Resources (ILAR). Subject information such as age, sex, and weight, and unique identifying numbers, are found in Table 1.

TABLE 1

Subject Information including animal ID, sex (male, M; female, F), weight (kg), birth date, study date, age (years), and time of PFT (hours post $O_3$ or air exposure).

| Group | Animal ID | Sex | Weight (kg) | Birth Date | Study Date | Age (yrs) | PFT time (hours post exposure) |
|---|---|---|---|---|---|---|---|
| LGM + air | 44145 | M | 5.82 | Mar. 21, 2014 | Dec. 7, 2017 | 3.72 | 15.5 |
|  | 44055 | M | 6.34 | Mar. 17, 2014 | Jan. 16, 2018 | 3.84 | 15 |
|  | 45324 | F | 3.92 | May 9, 2015 | Jan. 17, 2018 | 2.70 | 15.25 |
|  | 44307 | M | 7.45 | Apr. 17, 2014 | Feb. 2, 2018 | 3.80 | 15.15 |
|  | 45005 | F | 4.36 | Apr. 2, 2015 | Feb. 5, 2018 | 2.85 | 15.25 |
| placebo + O3 | 45356 | M | 3.84 | May 13, 2015 | Dec. 7, 2017 | 2.57 | 11.5 |
|  | 45230 | F | 4.11 | Apr. 28, 2015 | Jan. 16, 2018 | 2.72 | 13.5 |
|  | 45461 | M | 3.99 | Jun. 6, 2015 | Jan. 17, 2018 | 2.62 | 11.5 |
|  | 45440 | F | 5.04 | May 31, 2015 | Jan. 30, 2018 | 2.67 | 13.25 |
|  | 44951 | M | 4.78 | Mar, 26, 2015 | Feb. 2, 2018 | 2.86 | 13.25 |
|  | 45439 | F | 4.09 | May 31, 2015 | Feb. 5, 2018 | 2.69 | 11.5 |
| LGM + O3 | 44147 | M | 6.57 | Apr. 1, 2014 | Dec. 7, 2017 | 3.69 | 13.5 |
|  | 45006 | F | 5.02 | Apr. 2, 2015 | Jan. 16, 2018 | 2.79 | 11.5 |
|  | 45094 | F | 3.38 | Apr. 14, 2015 | Jan. 17, 2018 | 2.76 | 13.25 |
|  | 44365 | M | 7.02 | Apr. 22, 2014 | Jan. 30, 2018 | 3.78 | 11.45 |
|  | 44441 | M | 6.37 | May 1, 2014 | Feb. 2, 2018 | 3.76 | 11.5 |
|  | 45473 | F | 3.74 | Jun. 12, 2015 | Feb. 5, 2018 | 2.65 | 13.5 |
| Average |  |  |  |  |  |  |  |
| LGM + air |  | n = 3M | 5.6 |  |  | 3.4 | 15.2 |
| placebo + O3 |  | n = 3M | 4.3 |  |  | 2.7 | 12.4 |
| LGM + O3 |  | n = 3M | 5.4 |  |  | 3.2 | 12.5 |

Experimental Protocol & Sample Collection

NHPs were recruited to the study and randomly assigned to the LGM2605 air, placebo+$O_3$ or LGM2605+$O_3$ experimental groups and acclimated indoors for 1-3 days. When recruited, female NHPs were screened for pregnancy via ultrasound and excluded from the study if pregnant. During acclimation, NHPs were trained to accept LGM2605 or placebo in small treats (peanut butter sandwiches). Animals were fasted overnight before Day 0 baseline measurements and samples were taken [blood draw, BAL harvest, lung brushing, pulmonary function test (PFT)]. See FIG. 1 for detailed study design.

Animals were immobilized with an intramuscular injection of Ketamine (5-30 mg/kg), and a blood sample (up to 20 mL) was drawn from a peripheral vessel in accordance with veterinary staff guidelines. Following the blood draw, NHP's were further anesthetized using intravenous Propofol (10-30 mg/kg/hr) with the dose adjusted as deemed necessary by the attending veterinarian. NHPs were then intubated with an appropriate sized cuffed endotracheal tube. Static Lung Mechanics were measured in a whole-body plethysmograph (Buxco Electronics, Wilmington, N.C.). Sedated monkeys were connected to a 3-way valve assembly and given supplemental $O_2$ during the procedure. The semi-automated Maneuvers XA (Buxco Electronics) software controlled positive pressure inflation and negative pressure deflation to the lung in order to calculate the following parameters: standard static lung volumes/capacities, forced expiratory volumes and flows, quasi-static lung compliance, functional residual capacity and thoracic gas volume.

Airway responsiveness to aerosolized methacholine challenge was then performed in a head-out body plethysmopgraph (body box), with the intubation tube attached to a pneumatic four-way valve/pneumotachograph assembly. All challenges were administered as aerosols at a set inflation pressure and breathing frequency (10.0 cm $H_2O$ and 30.0 bpm) using a compressed air nebulizer (Vortran, Inc., Mini-heart Model) in series with a positive pressure ventilator (Bird Mark 7A respirator). Following baseline measurements and aerosolization of saline, methacholine challenge began at 0.0625 mg/mL, and doubled until a maximum concentration of 32 mg/mL was reached. The final concentration of aerosol delivered was the concentration that doubled the raw EC200 value or caused arterial oxygen saturation to fall below 70%. Pulmonary mechanics were evaluated using a transfer impedance method: Briefly, the monkeys breathed spontaneously through the pneumotachograph (Fleisch no. 2) while the thorax of the monkey was vibrated using a pseudo-random noise waveform encompassing frequencies of 2 to 128 Hz by two speakers mounted in the walls of the head-out plethysmograph (Pulmetrics Group, Boston, Mass.). The small changes in flow produced at the mouth were measured along with the changes in pressure inside the plethsmograph using a Microswitch transducer (model 743PC). This technique allowed the monkey to breathe spontaneously while making continuous pulmonary mechanics measurements. Concurrently, changes in lung compliance were assessed by placing either a fluid or air-filled balloon catheter in the esophagus at the level of the heart to measure transpulmonary pressure. Pressure/flow signals were collected and processed using a digital data acquisition system (PO-NE-MAH, Gould Instruments Inc) and lung compliance calculated for each dose of either methacholine.

Following PFT measurements, BAL was harvested by inserting a bronchoscope through the orotracheal tube into the trachea and then into the lung lobe and segment to be sampled. The camera attachment allowed us to define the exact location in the airway where samples were obtained by brushing and lavage. The end of the bronchoscope was wedged in a segmental or subsegmental bronchus and 2 cc/kg saline was instilled and aspirated back, for recovery of airway lining fluid. Approximately 50% of instilled fluid was recovered. A second aspiration was performed to obtain sufficient cells for analysis. BAL was performed immediately following the PFT. After BAL was collected, lung brushings were collected to gain epithelial cells from the affected airways. In brief, a flexible brush was passed through the bronchoscope and the bronchial surface was gently abraded to obtain bronchial epithelial cells.

While the animals were still sedated, a single 50 mg/kg dose of LGM2605 was administered via syringe Animals recovered from baseline procedures and were treated for the next 6 days with twice per day 25 mg/kg LGM2605 in peanut butter sandwiches. Following the final dose of LGM2605, animals were exposed to air or 0.3 ppm $O_3$ for 6.6 hours on Day 7. Approximately 12 hours later, all procedures described were repeated on Day 8.

After all procedures were completed on Day 8, animals were allowed to rest indoors overnight before being returned to their native outdoor field cage, or when deemed appropriate by the staff veterinarian. The University of California, Davis Institutional Animal Care and Use Committee approved the NHP experimental protocol #19997.

Clinical Reports

Detailed clinical reports were kept regarding any changes in animal health before enrollment to the study or after return to colony. Subject 45409 was enrolled in the study and had baseline measurements performed on Jan. 30, 2018. Laboratory personnel were notified by SRA that the subject showed no interest and would not take LGM2605 in the treat given to all animals following his baseline measurements on Jan. 30, 2018. Laboratory personnel suggested that LGM2605 be given by syringe directly into the animal's mouth, and while this method of dosing was adhered to for 2 days, the animal did not accept this form of dosing well, and it was noted by SRA that the animal would not swallow the LGM2605 given by syringe. On Feb. 2, 2018, the SRA reported that MMU45409 was not eating well. On vet exam, the animal had rectal prolapse and appeared dehydrated. Subcutaneous fluids (LRS) were administered, and the animal was started on dietary supplements and oral electrolytes. Per request of Study Director, more intensive therapies were not implemented on the day of presentation. On Feb. 3, 2018, the animal remained inappetant and dehydrated. A blood test (Nova) confirmed dehydration with minor electrolyte imbalances. The animal received IV and SQ fluids cageside. On Feb. 4, 2018, the animal was noted to be depressed (sitting hunched in cage), inappetant, and dehydrated. The animal was sedated. A PE revealed skin pustules, thin body condition, and evidence of diarrhea. Labs confirmed dehydration with more significant electrolyte abnormalities. The animal was treated with IV and SQ fluids, cefazolin (antibiotic for skin infection), enrofloxacin (antibiotic for diarrhea), and flunixin meglumine (a pain medication to target GI pain). Rectal and skin cultures were obtained (ultimately revealing *Campylobacter lari*, a GI commensal of questionable pathogenicity and *Staphylococcus* spp, a normal skin organism). The CBC obtained on Feb. 4, 2018 revealed significant infection w/left shift (27.7 WBC, 8% band neutrophils) consistent with pathogenic diarrhea. Recheck electrolytes on Feb. 5, 2018 showed improvement and hydration was adequate. The animal's attitude and appetite began to improve on Feb. 6, 2018. Reports of liquid stool persisted until Feb. 8, 2018 although the animal's hydration was normal. Antibiotic treatment continued until Feb. 12, 2018, and the animal was discharged back to the homecage on Feb. 13, 2018. This animal's removal was deemed unrelated to any treatment by LGM2605.

PBMC Isolation

Blood collected from NHPs was diluted 1:1 in 1×PBS+ 2% FBS. The NHP blood mixture was carefully layered over Lymphoprep density gradient (STEMCELL Technologies, Vancouver, Canada) in 15 mL conical tubes. The cell density gradient was then centrifuged at 800×g at 20° C. for 20 minutes, with the centrifuge brake and acceleration speed set to 0. PBMCs were harvested from the interphase layer and washed twice with ice cold PBS. Cells were counted via the Countess® Automated Cell Counter (Thermo Fisher Scientific, Waltham, Mass.) then apportioned for downstream flow cytometry and fluorescent activated cell sorting (FACS)

experiments. $1\times10^6$ PBMCs were snap frozen and stored at −80° C. in TRIzol Reagent (Thermo Fisher Scientific, Waltham, Mass.).

Serum Collection

Blood was allowed to clot for at least 30 minutes at room temperature. Serum collection tubes were centrifuged at 1,500×g for 10 minutes to remove the clot. Supernatant was harvested, snap frozen, and stored at −80° C.

BAL Cells and Supernatant

Harvested BAL was centrifuged to separate cells and supernatant. Supernatant derived from the first aspiration of saline was aliquoted, snap frozen, and stored at −80° C. Supernatant derived from the second and third aspirations of saline was pooled, then aliquoted, snap frozen, and stored at −80° C. Cells from all aspirations were pooled. Cells were counted via the Countess® Automated Cell Counter (Thermo Fisher Scientific, Waltham, Mass.). Approximately 50,000 cells were cytospun and stained with Shandon™ Kwik-Diff™ Stain (Thermo Fisher Scientific, Waltham, Mass.). Differential cell count was performed at 400× objective under a light microscope to determine the proportion and absolute number of macrophages, lymphocytes, neutrophils, and eosinophils present in the airway after LGM2605 treatment or air/$O_3$ exposure. The remaining cells were apportioned for downstream flow cytometry experiments.

PerCP/Cy5.5 (clone HP-3G10), CD4-FITC (clone A161A1), CD8a-APC/Cy7 (clone RPA-T8), HLA-DR-APC/Cy7 (clone L243), CD11c− Pacific Blue (clone 3.9), CD123-PE (clone 6H6), CD16-PerCP/Cy5.5 (clone 3G8), CD1c-Alexa Fluor 488 (clone L161), CD40-PE-Cy7 (clone HB14), IL-4-PE (clone MP4-25D2), IFNγ-PE-Cy7 (clone B27). Anti-human Abs purchased from BD Biosciences included: CD3-Alexa Fluor 488 (clone SP34-2), CD56-Alexa Fluor 488 (clone B159), CD90-APC (clone 5E10), CD45-PE-CF594 (anti-NHP, clone D058-1283). CD336 (NKp44)-PE (clone Z231) was purchased from Beckman Coulter. CD127-PE-Vio770 (clone MB15-18C9) was purchased from Miltenyi Biotec.

PBMC and BAL single cell suspensions were stained with Live Dead for 15 minutes in the dark. BAL cell suspensions were then blocked with serum for 5 mins PBMC and BAL single cell suspensions were stained for surface antigens for 30 minutes at 4° C. in the dark. Cells were fixed and permeabilized using the BD Cytofix/Cytoperm kit (BD Biosciences, San Jose, Calif.) and stained for intracellular antigens for 40 minutes at 4° C. in the dark. Acquisition of all samples was performed LSR II or Fortessa (BD, Franklin Lakes, N.J.). Data were analyzed using FlowJo v9.6 software (Tree Star Inc., Ashland, Oreg.) as we previously described (27). Lineage markers for NHP ILCs included: CD3, CD14, CD16, CD19, and CD56. Specific flow panels and voltages can be found in Table 2.

TABLE 2

Flow Cytometry Panels and Voltages.

| ILC2/3 panel | | | DC Panel | | | T cell pannel | | |
|---|---|---|---|---|---|---|---|---|
| Color | Antigen | Voltage | Color | Antigen | Voltage | Color | Antigen | Voltage |
| FITC | CD3 | 400 | FITC | CD1c | 400 | FITC | CD4 | 400 |
|  | CD14 |  | PE | CD123 | 467 | APC | CD3 | 500 |
|  | CD16 |  | PCP-Cy5.5 | CD16 | 450 | PE-CF594 | CD45 | 350 |
|  | CD20 |  | P7 | CD40 | 450 | APC-Cy7 | CD8 | 350 |
|  | CD56 |  |  | PE-CF594 | CD45 | 350 | PB | CD25 | 400 |
| PE | NKp44 | 467 | APC-Cy7 | HLA-DR (clone L243) | 350 | BV510 | L/D | 350 |
| PCP-Cy5.5 | CD161 | 450 | PB | CD11c | 400 |  |  |  |
| P7 | CD127 | 450 | BV510 | L/D | 350 | PE | IL-4 | 467 |
| APC | CD90 | 500 |  |  |  | P7 | IFNg | 450 |
| APC-Cy7 | ckit (CD117) | 350 | APC | TNFα | 500 |  |  |  |
| PB | CD25 | 400 |  |  |  |  |  |  |
| BV510 | L/D | 350 |  |  |  |  |  |  |

Lung Brushing

Lung brushings were vortexed in a cryovial containing 1×PBS for 1 minute to detach the cells from the brush. The harvested cells were then aliquoted, snap frozen, and stored at −80° C. in TRIzol Reagent (Thermo Fisher Scientific, Waltham Mass.).

Flow Cytometry

Flow cytometry experiments were performed on BAL and peripheral blood cells. Approximately 1 million PBMCs were apportioned for the T cell panel, 2 million PBMCs to the DC panel, and 10 million PBMCs to the ILC panel. 20% of the BAL cells were apportioned to the T cell panel, 30% to the DC panel, and 50% to the ILC panel. Abs were purchased from Biolegend (San Diego, Calif.), BD Biosiences (San Jose, Calif.), eBioscience (San Diego, Calif.), Beckman Coulter (Brea, Calif.), and Miltenyi Biotec (Bergisch Gladbach, Germany)

Single cell suspensions of isolated PBMCs were stained with the following anti-human Abs purchased from Biolegend: CD14-FITC (clone M5E2), CD16-FITC (clone 3G8), CD20-FITC (clone 2H7), CD117(c-kit)-APC/Cy7 (clone 104D2), CD25-Pacific Blue (clone M-A251), CD161-

Cell Sorting

The remaining PBMCs not processed for direct flow cytometry experiments or stored in TRIzol were apportioned for cell sorting experiments. ILC2s were isolated via fluorescence activated cell sorting directly into TRIzol Reagent (Thermo Fisher Scientific, Waltham, Mass.), then snap frozen and stored at −80° C. ILC2s were identified as Lineage−CD90+CD25+ckit(var) cells.

qPCR

For qPCR analysis of NHP blood ILC2s, RNA was extracted using the Direct-zol RNA MicroPrep Kit. 70 ng total RNA was reverse transcribed using the QuantiTect Reverse Transcription Kit (Qiagen, Hilden, Germany) For qPCR analysis of NHP lung brushings, RNA was extracted from TRIzol via the chloroform separation method following manufacturer's instructions. 70 ng RNA was reverse transcribed into cDNA via the High-Capacity cDNA Reverse Transcription Kit (Thermo Fisher Scientific, Waltham, Mass.). Fold change was calculated using the ΔΔCt method, first normalizing values to the geometric mean of GAPDH and RPL32, then to Day 1 as appropriate.

qPCR was performed on cDNA using SYBR green reagents (Applied Biosystems, Foster City, Calif.) on a ViiA 7 Real-Time PCR System (Thermo Fisher Scientific, Waltham Mass.).

Western Blot

BAL SP-D was detected via SDS and Native-PAGE western blot. Total protein in the BAL was quantified via Pierce BCA Protein Assay Kit (Thermo Fisher Scientific, Waltham, Mass.). 1 µg total BAL protein was run under standard reducing or native gel electrophoresis conditions using NuPAGE™ MOPS SDS Running Buffer (Thermo Fisher Scientific, Waltham, Mass.) or 1× Novex Tris-Glycine Native Running Buffer (Thermo Fisher Scientific, Waltham, Mass.). The gel was transferred to a mini Nitrocellulose membrane using the iBlot® gel transfer mini stacks (Thermo Fisher Scientific, Waltham, Mass.). The membrane was probed with mouse anti-SP-D 1:1,000 (in-house 10F6E12 monoclonal) followed by goat anti-mouse conjugated HRP 1:3,000 (Santa Cruz Biotechnology, Santa Cruz, Calif.), then activated via Pierce™ ECL Western Blotting Substrate (Thermo Fisher Scientific, Waltham, Mass.).

Data Analysis

Statistical analysis was performed using Prism v7 software (GraphPad Inc., La Jolla, Calif.). Paired t-test was used for comparisons between Day 1 and Day 8 as indicated in the figures. Linear regression was used to calculate Pearson correlation coefficient (R) and goodness of fit (p) for correlation plots. Data are expressed as mean±SEM unless otherwise specified. $p<0.05$ was considered statistically significant.

Results

LGM2605 Treatment Prevented Inflammation and AHR Induced by O3.

The two major effects of ozone inhalation are pulmonary AHR and inflammation (1). In part, ozone is thought to induce inflammation and AHR by causing oxidative stress in the airways (7, 25). LGM2605, a synthetic lignan secoisolariciresinol diglucoside, is an anti-inflammatory compound that increases that expression of Nrf2, a transcription factor that regulates the expression of antioxidant genes (20, 26). While the innate inflammatory and functional effects of ozone on the lung have been studied extensively in mice, it is not clear if similar mechanisms regulate the effects of ozone in primates. We investigated if ozone exposure caused pulmonary inflammation and AHR in rhesus macaques (*Macaca mulatta*) (FIG. 1). In addition, we determined if oral treatment of LG2605 for 7 days could dampen the inflammation or AHR induced by ozone inhalation (FIG. 1).

Figures 2A, 2B, 2C, 2D:
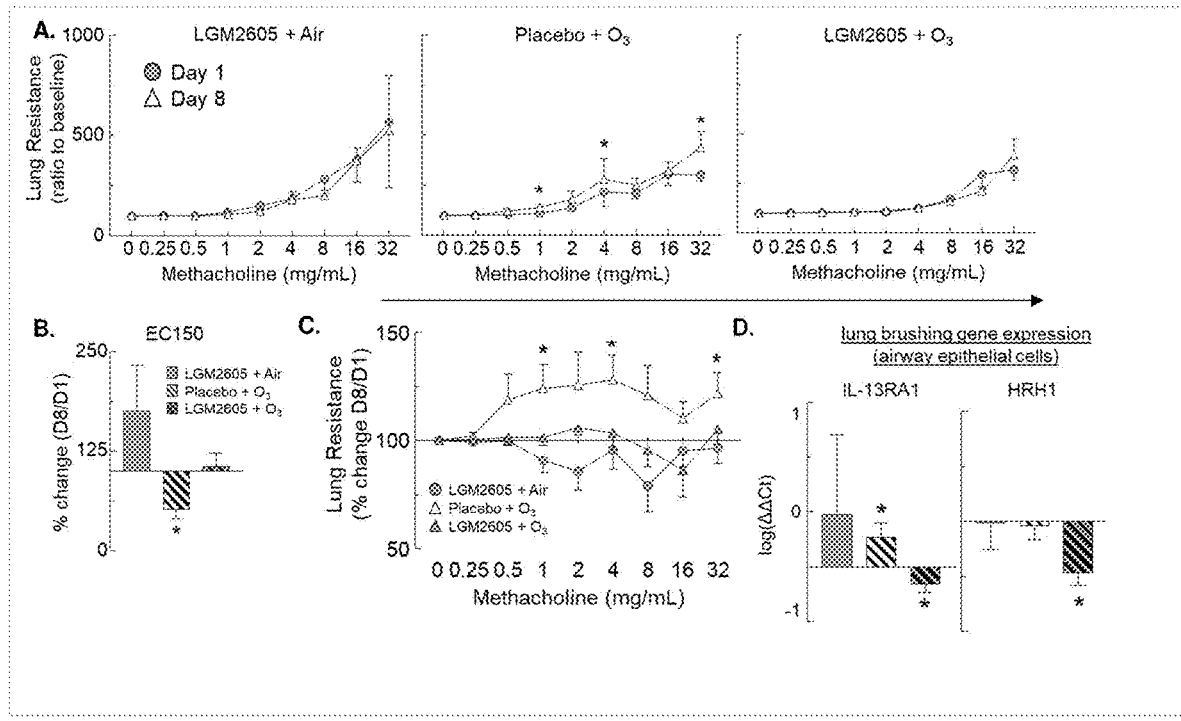
FIGS. 2A-2D illustrate that LGM2605 treatment prevented $O_3$-induced AHR.

We recruited rhesus macaques from the California National Primate Research Center and collected baseline measurements of inflammation and AHR. Following 7 days treatment with LGM2605 or placebo and exposure to 0.3 ppm $O_3$ or air, the same inflammatory and AHR endpoints were recorded. Lung resistance was measured in response to increasing concentrations of methacholine aerosolized into the airways. We determined that at 1, 4, and 32 mg/mL, there was significant increase in lung resistance on day 8 compared to day 1 in placebo+$O_3$ animals (FIG. 2A). There were no significant differences noted between day 1 and day 8 at any dose of methacholine for LGM2605+ air or LGM2605+$O_3$ animals (FIG. 2A). The effective concentration of methacholine that raised lung resistance by 150% (EC150) was calculated on day 1 and day 8 for each animal. The EC150 was significantly reduced in placebo+$O_3$ animals, while there was no change in EC150 in LGM2605+$O_3$ animals (FIG. 2B). There was a trend for an increase in EC150 for LGM2605+ air animals, although this was not significant due to variability in responsiveness to LGM2605 in this experimental group (FIG. 2B). When day 8 lung resistance values from the dose response curves generated in FIG. 2A were normalized to day 1 for each animal, it was determined that at 1, 4, and 32 mg/mL there was a significant increase in lung resistance in placebo+$O_3$ animals, confirming our findings (FIG. 2C). Gene expression of IL-13RA1 and HRH1, receptors involved in AHR, were studied in response to LGM2605 treatment and $O_3$ exposure. IL-13RA1 was induced by $O_3$ exposure, while IL-13RA1 and HRH1 were inhibited by LGM2605 treatment prior to $O_3$ exposure (FIG. 2D). This suggests that IL-13 signaling is involved in the functional response of the lung to $O_3$ and LGM2605. We studied pulmonary inflammation in response to LGM2605 treatment and $O_3$ or air exposure, since this is another major effect of ozone inhalation.

Figures 3A, 3B, 3C, 3D:
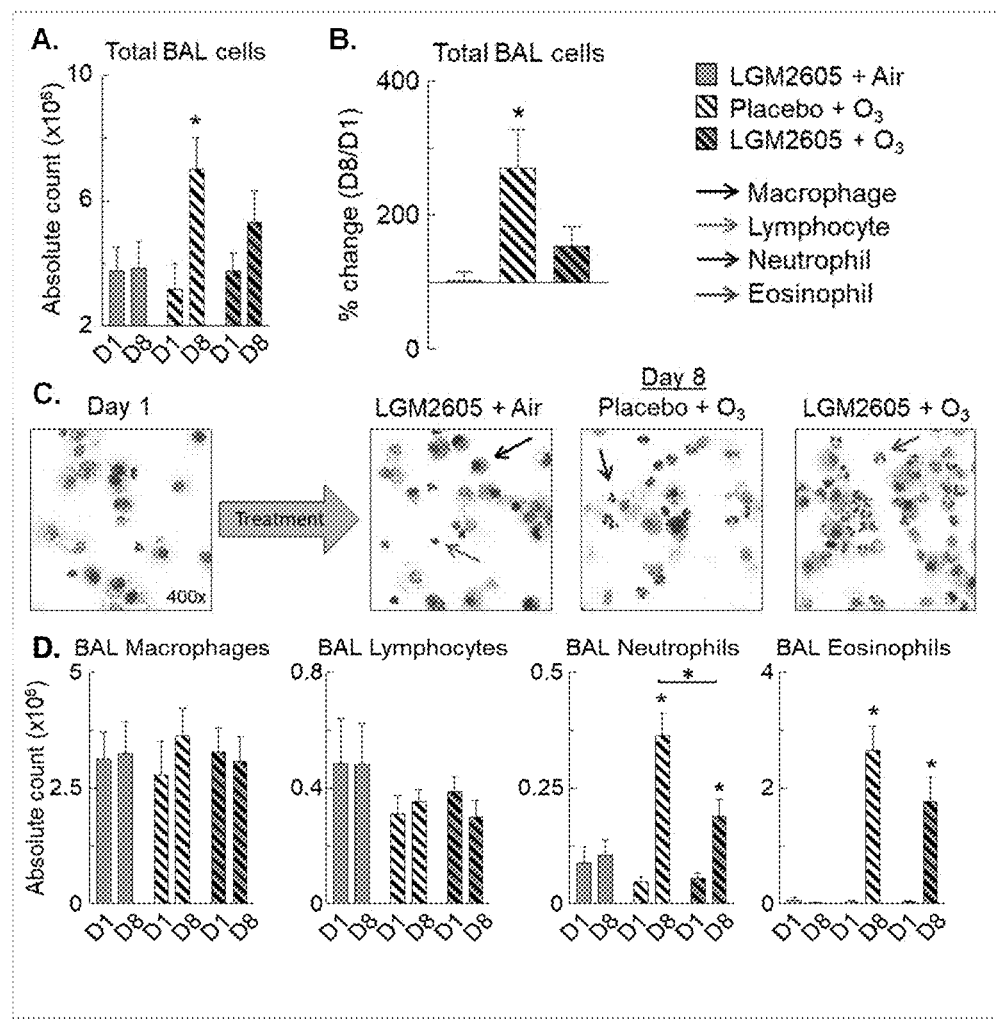
FIGS. 3A-3D illustrate that LGM2605 treatment prevented $O_3$-induced inflammation.
Figure 4:
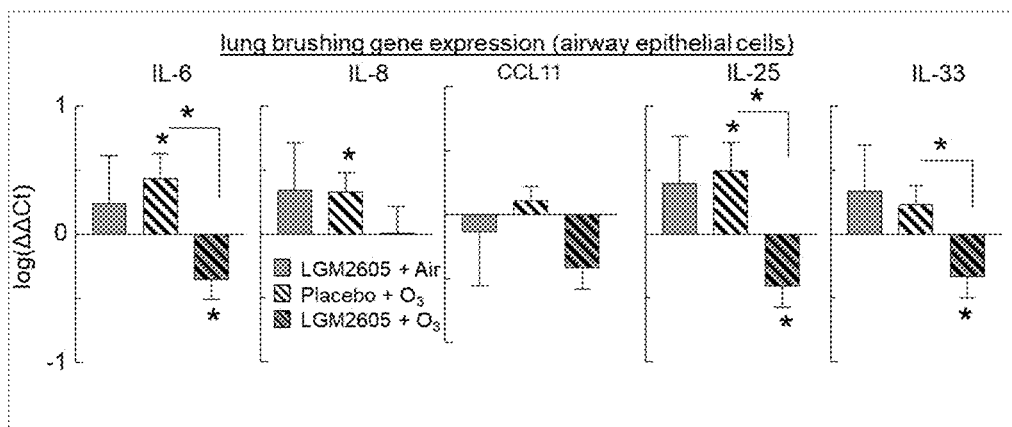
FIG. 4 illustrates that LGM2605 protected from $O_3$-induced IL-6, IL-25, and IL-33 in airway epithelial cells. RNA was reverse transcribed lung brushings. log($\Delta\Delta Ct$) values were calculated first to the geometric mean of GAPDH/RPL32, then to day 1 for each animal.

BAL was harvested from the airways of non-human primates and total cells were quantified. There was no difference between the total number of BAL cells on day 1 and day 8 in animals treated with LGM2605 and exposed to air (FIGS. 3A-3B). In placebo+$O_3$ animals, there was a significant increase in the total number of cells in the BAL on day 8 compared to day 1 (FIGS. 3A-3B). Treatment with LGM2605 prior to $O_3$ exposure protected from an increase in total BAL cells (FIGS. 3A-3B). In mice, the primary inflammatory cell present in the airways following $O_3$ exposure is the neutrophil. We tested if $O_3$ induced inflammation in non-human primates was represented by neutrophils, or if there were other inflammatory cells present in the airways following exposure. Cytospins of BAL cells were stained and viewed under a light microscope. At day 1, the vast majority of BAL cells were determined to be macrophages (black arrows), while approximately 10% of cells were lymphocytes (green arrows) and 2-3% of cells were neutrophils (blue arrows) (FIG. 3C). LGM2605 treatment and air exposure caused no appreciable difference in the composition of BAL cells (FIG. 3C). When cytospins were viewed, it was apparent that $O_3$ exposure caused an influx of neutrophils and eosinophils (red arrows) to the BAL (FIG. 3C). When quantified, it was determined that LGM2605 treatment and $O_3$ exposure caused no significant change in the number of macrophages or lymphoyctes present in the airways (FIG. 3D). $O_3$ exposure caused a significant increase in the number of neutrophils and eosinophils present in the BAL (FIG. 3D). BAL neutrophilia, but not eosinophilia, was significantly reduced in LGM2605+$O_3$ compared to placebo+$O_3$ animals Although BAL eosinophilia was reduced in LGM2605+$O_3$ compared to placebo+$O_3$ animals, this was not statistically significant. IL-6 and IL-8 are pro-inflammatory cytokines released immediately following $O_3$ inhalation. In airway epithelial cells derived from lung brushings, we discovered that $O_3$ induced IL-6 and IL-8 gene expression, while treatment with LGM2605 prior to $O_3$ exposure prevented such increases (FIG. 4). The reduction in IL-8 expression was comparable to the reduction in neutrophilia in LGM2605+$O_3$ exposure animals, suggesting that decreased expression of the prominent neutrophil chemokine (IL-8) reduced neutrophilia CCL11, a chemokine critical for BAL eosinophilia was not significantly altered in any experimental group (FIG. 4).

$O_3$ Inhalation Heightened ILC2 Immunity in the Airways.

Figure 11:
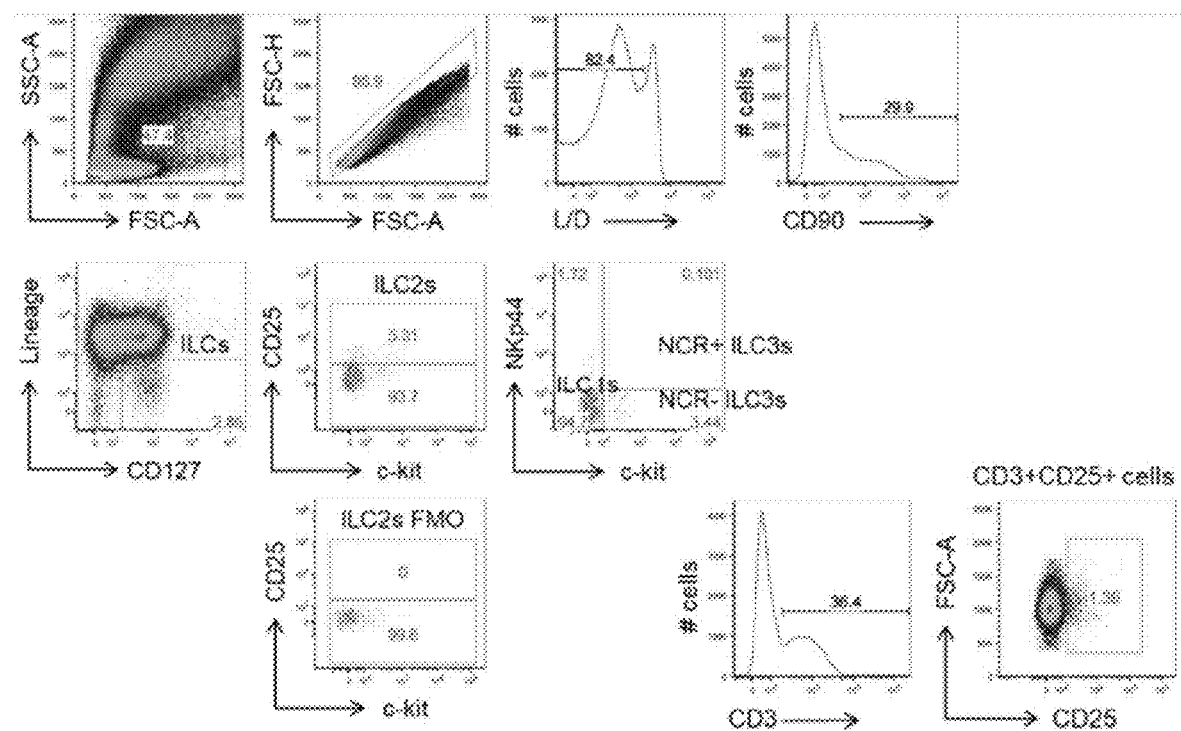
FIG. 11 illustrates a ILC gating strategy with FMO control and CD3+CD25+ control.

The innate immune system in the lung plays a key role in initiating inflammation and AHR following $O_3$ inhalation. In mice, $O_3$ induced the expression of the so-called "alarmin" cytokines (IL-33, IL-25, TSLP) in the airways, stimulating the activation of pulmonary ILC2s. ILC2s regulate $O_3$ induced inflammation and AHR in mice. We investigated if pulmonary ILC2s in non-human primates were sensitive to LGM2605 treatment and $O_3$ exposure via flow cytometry. We hypothesized that $O_3$ would increase the number of ILC2s in the airways, independent of LGM2605 treatment. We determined if effects on ILC2s were exclusive to the lung by studying changes in cells derived from the peripheral blood. ILC2s have not been studied before in non-human primates, so we developed a flow cytometry method based on studies in humans to examine these elusive cells (FIG. 11, innate lymphoid cell gating strategy). ILCs from the BAL and peripheral blood were defined as live CD90+ Lineage−CD127+ cells; ILC1s were defined as CD25−ckit−NKp44− ILCs; ILC2s were defined as CD25+ckit(var) ILCs; NCR− ILC3s were defined as CD25−ckit+NKp44− ILCs; NCR+ ILC3s were defined as CD25−ckit(var) NKp44+ ILCs (FIG. 11).

Figures 5A, 5B, 5C:
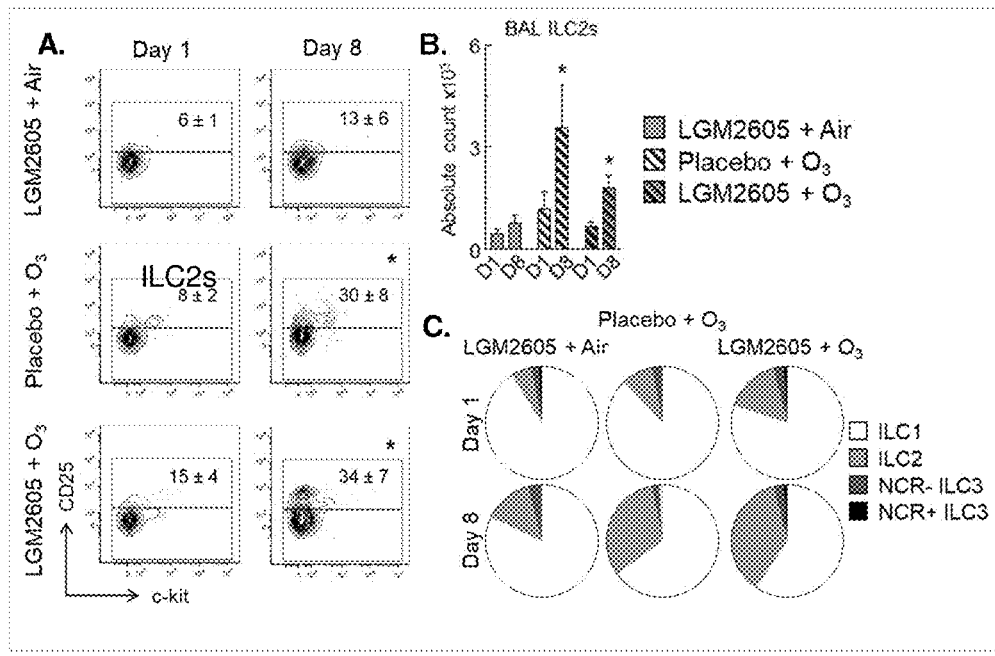
FIGS. 5A-5C illustrate $O_3$ inhalation heightened ILC2 immunity in the airways.
Figures 6A, 6B:
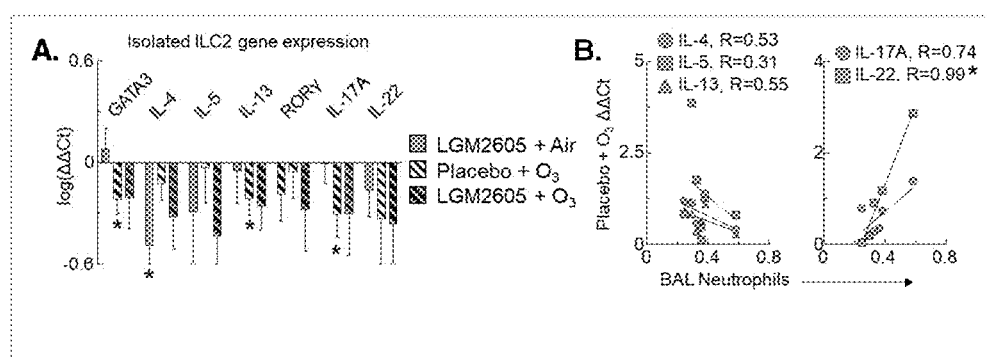
FIGS. 6A-6B illustrate that $O_3$ exposure altered gene expression in blood ILC2s.
Figures 12A, 12B, 12C:
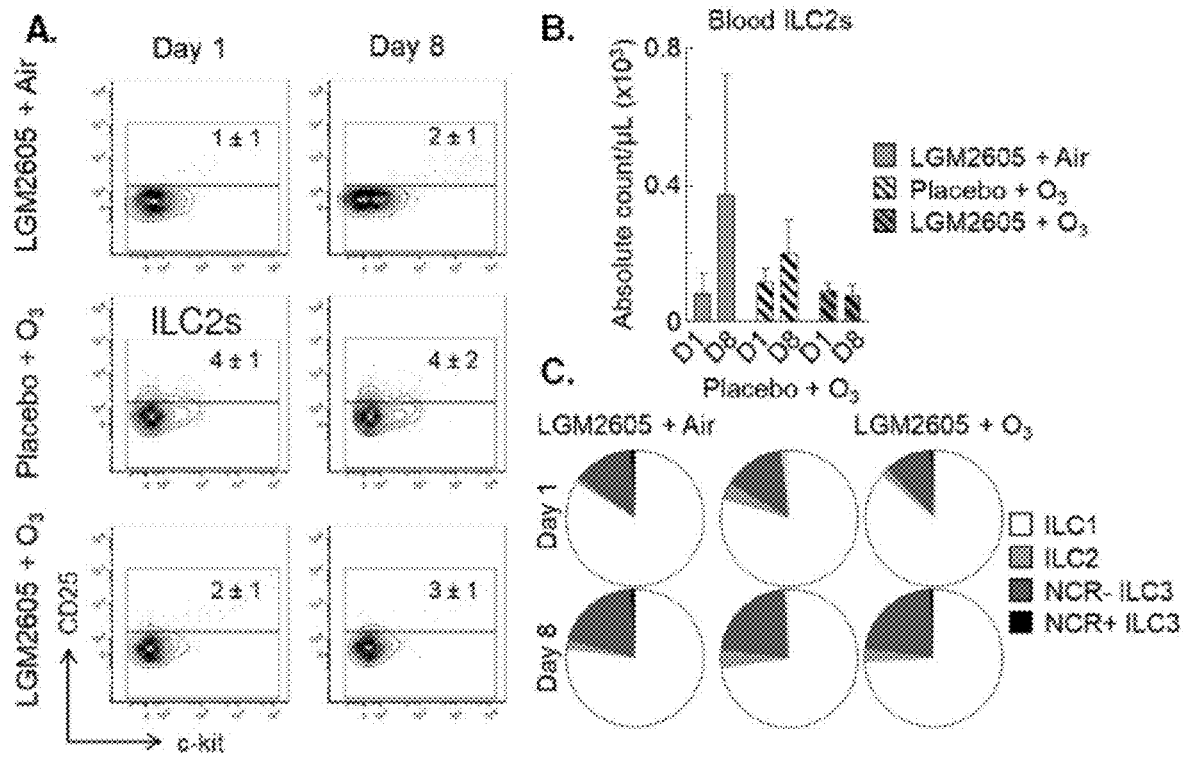
FIGS. 12A-12C illustrate that LGM2605 treatment and $O_3$ had no impact on ILC immunity in the peripheral blood.

$O_3$ significantly increased the proportion and absolute number of ILC2s and decreased the proportion of ILC1s in the BAL, independent of LGM2605 treatment (FIG. 5A-C). While BAL ILC2s were significantly increased in LGM2605+$O_3$ treated animals, they were non-significantly reduced compared to placebo+$O_3$ animals. This is consistent with the therapeutic benefit of LGM2605 on IL-33 and IL-25 gene expression in the airway epithelium. There were no changes in BAL ILCs in LGM2605 treated air exposed animals (FIG. 5B). Interestingly, we found that the shift in ILC2 representation in the BAL was specific to the airways, as the only ILC3 population increased in the peripheral blood in response to $O_3$ was NCR− ILC3s (FIGS. 12A-12C). We detected decreased expression of GATA3, IL-13, and IL-17A mRNA in isolated blood ILC2s from placebo+$O_3$, (FIG. 6A). There were no significant changes in gene expression in LGM2605+$O_3$ animals, but IL-4 was decreased in LGM2605+ air animals (FIG. 6A). Changes in gene expression of cytokines in placebo+$O_3$ blood ILC2s was correlated to BAL neutrophilia We found that IL-17A and IL-22 positively correlated to BAL neutrophilia, while IL-4, IL-5, and IL-13 negatively correlated to BAL neutrophilia (FIG. 6B). This suggests that $O_3$ induced changes gene expression of neutrophil promoting cytokines (IL-17A and IL-22) may play a role in regulating the pulmonary neutrophilic response, but Th2 cytokines (IL-4, IL-5, and IL-13) may not.

$O_3$ Inhalation Heightened CD1c+ Myeloid and CD123+ Plasmacytoid DC Immunity in the Airways.

Figures 7A, 7B, 7C, 7D, 7E, 7F:
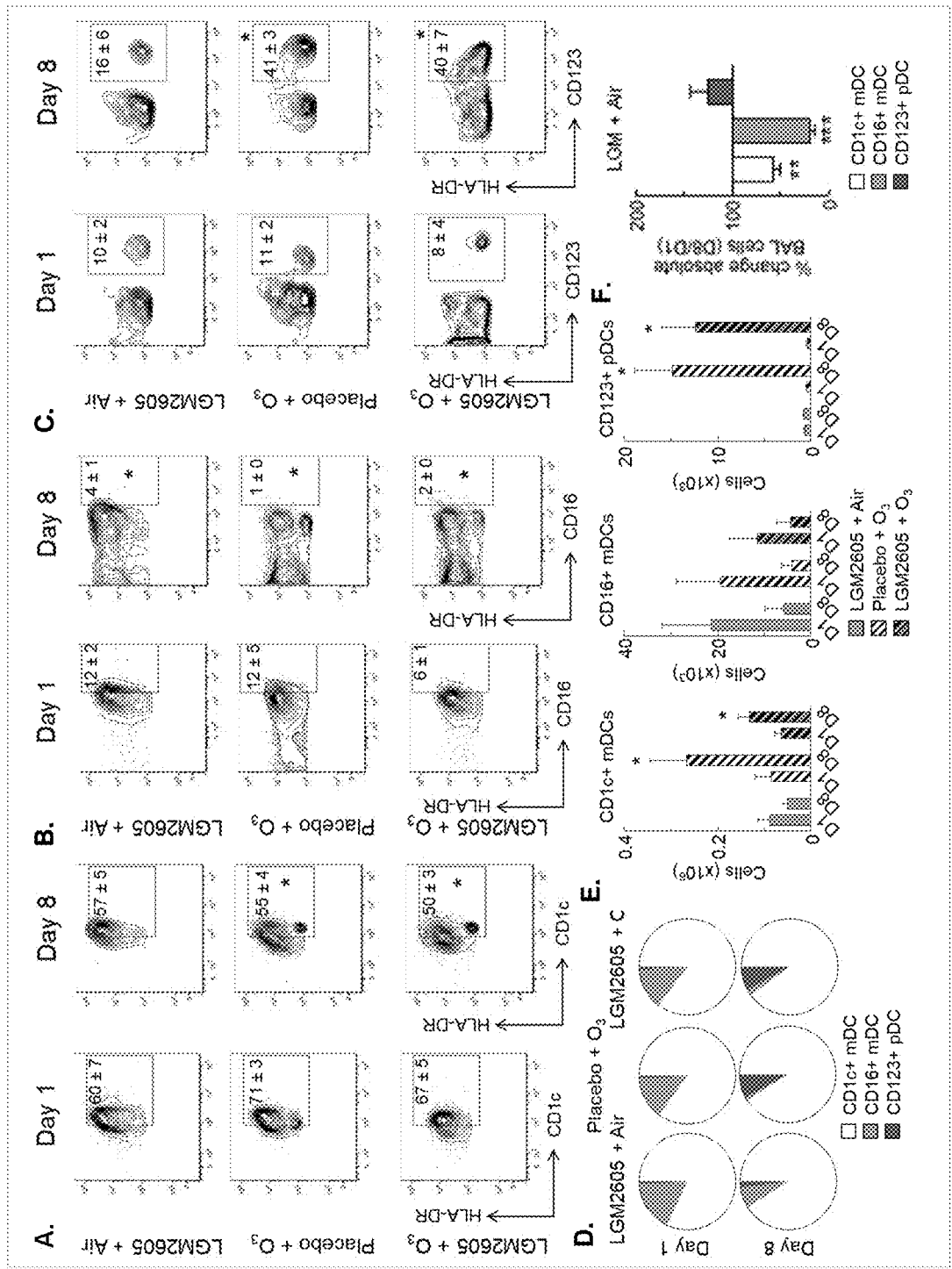
FIGS. 7A-7F illustrate that $O_3$ inhalation reduced mDC and increased pDC representation in the BAL.
Figure 13:
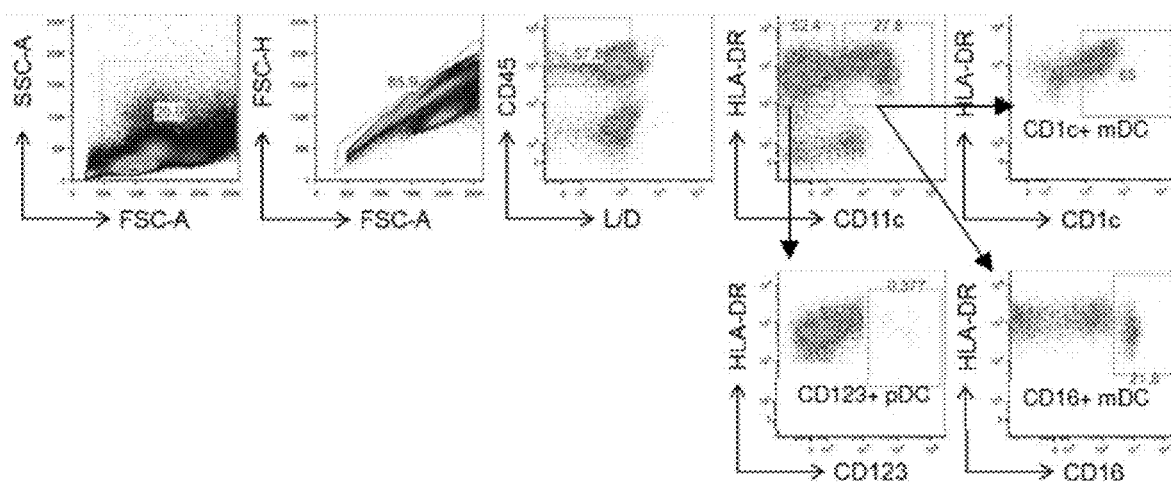
FIG. 13 illustrates a DC gating strategy.
Figures 14A, 14B, 14C, 14D:
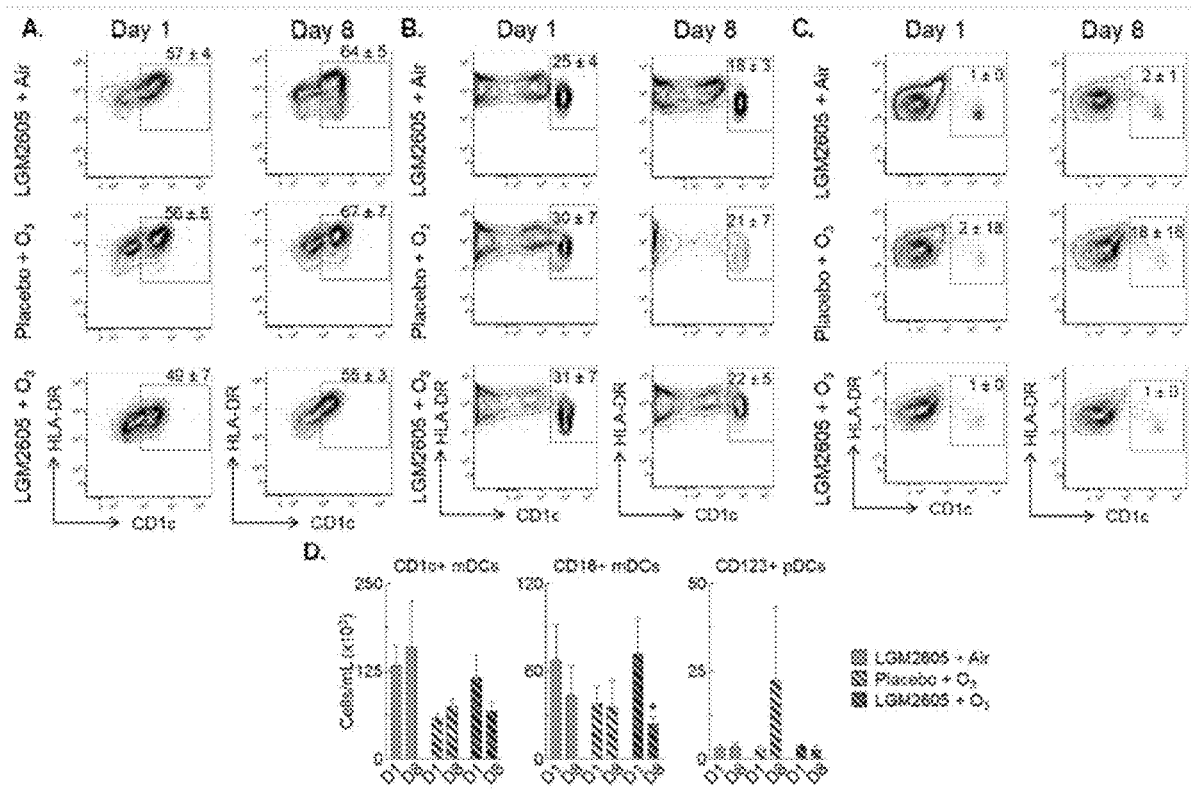
FIGS. 14A-14D illustrate that LGM2605 treatment and $O_3$ inhalation caused minor changes in blood DCs.

Dendritic cells (DCs) are the link between the innate and adaptive immune system. Indeed, studies have shown that ILCs influence the function of DCs, which in turn instruct the adaptive immune system. In allergen-induced inflammation, DCs are the key cellular link between ILC2 activation and Th2 cell immunity. Moreover, presence of DCs is required for optimal development of ILCs, suggesting that these two cell types critically influence each other. In response to $O_3$ inhalation in mice, DCs are quickly activated and produce TNFα to regulate the pulmonary response. Subsets of DCs carry out specific functions in the context of the lung (35). Myeloid DCs (CD11c+mDCs) initiate Th1 responses via IL-12 mediated activation, and stimulate IFNγ production by Th1 cells. CD1c+mDCs mainly induce chemotaxis of cells by production of IL-8, while CD16+ mDCs are pro-inflammatory as they produce TNFα and IL-1β, but less IL-8. On the other hand, CD123+ plasmacytoid DCs (CD11c− pDCs) initiate Th2 responses by stimulating IL-4 and IL-5 in Th2 cells, and produce IL-8 and TNFα themselves. pDCs are rare in number and don't perform typical DC functions, as they are poor at phagocytosis and antigen presentation. We investigated if BAL and blood DCs were sensitive to LGM2605 treatment and $O_3$ exposure. We hypothesized that DCs would be sensitive to $O_3$ exposure, but not LGM2605 treatment, similar to our findings in ILC2s. DC subsets were identified in the peripheral blood and BAL via flow cytometry as follows: CD1c+ mDCs were defined as live CD45+CD11c+HAL−DR+ CD1c+ cells; CD16+mDCs were defined as live CD45+ CD11c+HAL−DR+CD16+ cells; CD123+ pDCs were defined as live CD45+CD11c−HAL−DR+CD123+ cells (FIG. 13). Independent of LGM2605 treatment, $O_3$ inhalation significantly reduced the proportion of CD1c+mDCs present in the BAL (FIG. 7A). Interestingly, the proportion of CD16+mDCs in the BAL was reduced by treatment with LGM2605 and $O_3$ exposure (FIG. 7B). As $O_3$ shifted the DC profile in the BAL away from mDC representation, the proportion of CD123+ pDCs significantly increased in response to $O_3$ exposure and independent of LGM2605 treatment (FIG. 7C). These changes in relative representation of CD1c+mDCs, CD16+mDCs, and CD123+ pDCs are also visualized by parts of whole charts (FIG. 7D). While $O_3$ exposure reshaped the proportion of DCs in the BAL as determined by flow cytometry, quantification of such cellular changes revealed a more complex story. $O_3$ inhalation, independent of LGM2605 treatment, caused a significant increase in CD123+ pDCs in the BAL as expected, but also increased the number of CD1c+mDCs in the BAL (FIG. 7E). These changes occurred in conjunction with a reduction in CD16+mDCs in the BAL that did not reach statistical significance (FIG. 7E). LGM2605 treatment alone caused a significant reduction in the number of CD1c+mDCs and CD16+mDCs in the BAL (FIG. 7F). These findings suggest that LGM2605 treatment alone may dampen Th1 immunity by reducing mDC numbers in the airways, while $O_3$ exposure heightens Th2 immunity and reduces Th1 immunity by increasing pDC representation and altering mDC representation in the BAL. The changes in DC numbers induced by LGM2605 treatment or $O_3$ exposure were largely specific to the lung, however there were subtle changes discovered in the peripheral blood. LGM2605 treatment and $O_3$ exposure had no significant effects on CD1c+ mDC, CD16+ mDC, and CD123+ pDC proportions in the blood (FIGS. 14A-14C). In LGM2605 treated $O_3$ exposed animals, we detected a significant reduction in the number of circulating CD16+ mDCs (FIG. 14D), consistent with our CD16+ mDC findings in the BAL.

$O_3$ Inhalation Activated and Increased CD4+ T Cell Numbers in the Airways.

Figures 8A, 8B, 8C, 8D, 8E:
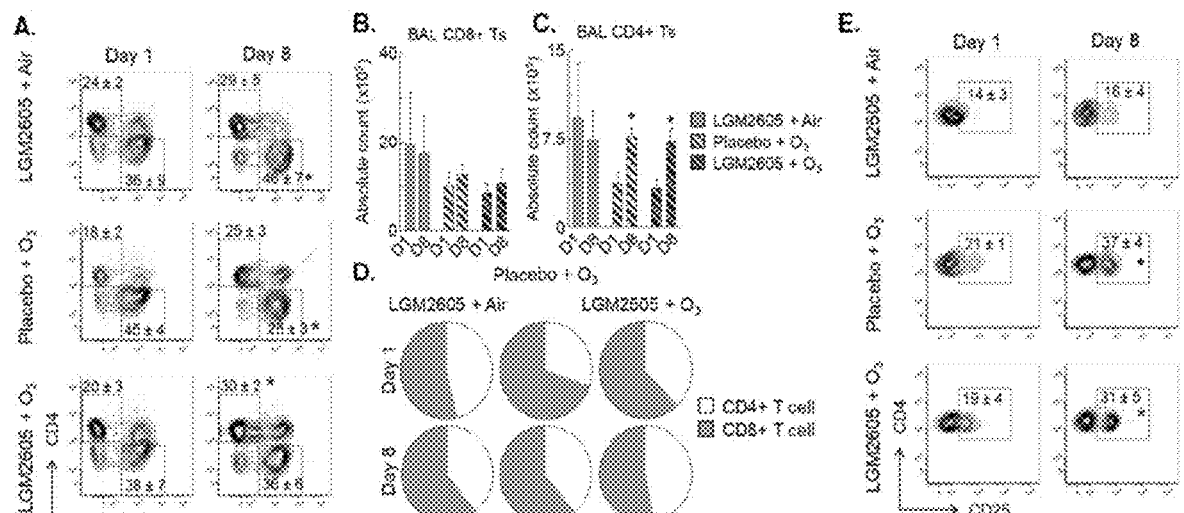
FIGS. 8A-8E illustrate that $O_3$ inhalation activated and increased CD4+ T cell numbers in the airways.
Figure 15:
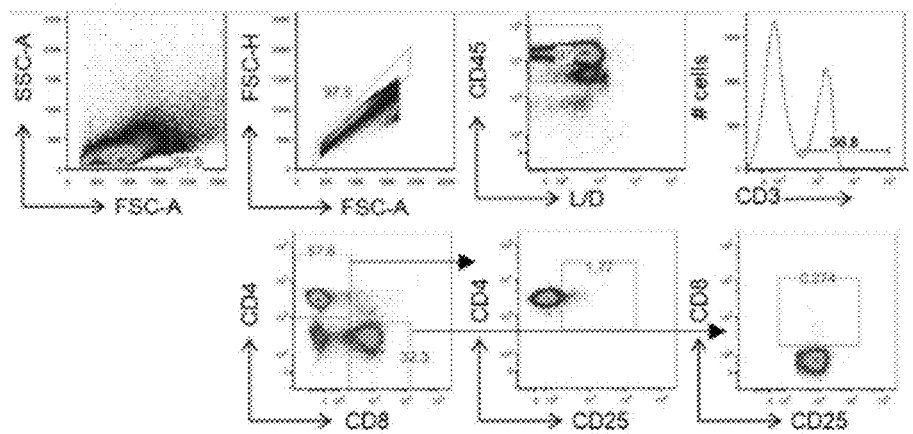
FIG. 15 illustrates a T cell gating strategy.
Figures 16A, 16B, 16C, 16D:
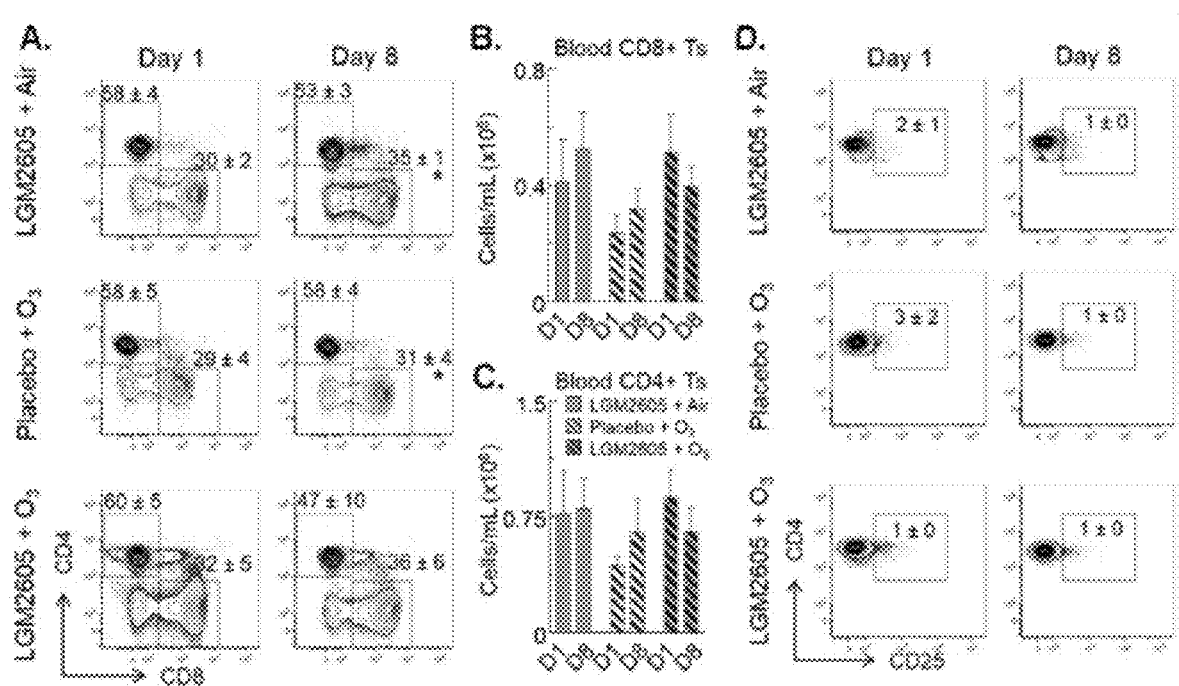
FIGS. 16A-16D illustrate that LGM2605 or $O_3$ alone increased the proportion of CD8+ T cells in the blood.

In this study, we demonstrated that $O_3$ exposure increased ILC2, CD1c+ mDC and CD123+ pDC numbers in the airways independent of LGM2605 treatment. Increased numbers of ILC2s and DCs would suggest heightened Th2 immunity, as these immune cells are critical initiators of Th2 responses. The role of the T cell response in regulating the pulmonary effects of $O_3$ exposure is controversial. Indeed, rodent models of $O_3$ exposure have offered conflicting reports on the nature of T-cell mediated inflammation and AHR induced by $O_3$. Previously, it was demonstrated that Th2 cells were not activated in response to $O_3$ exposure in mice, while others have demonstrated that γδ T cells play a key role in regulating the neutrophilic response to $O_3$. Non-human primates at CNPRC, however, are housed outdoors and exposed to environmental factors similar to humans. We discovered that the inflammatory response to $O_3$ in non-human primates was predominantly eosinophilic in nature. This stands in contrast to rodent models, which consistently demonstrate pulmonary inflammation dominated by neutrophils in response to $O_3$ alone, however $O_3$ in combination with allergen enhances eosinophilia in mice. Thus, we studied if T cells were impacted by $O_3$ inhalation or LGM2605 treatment in non-human primates. We hypothesized that CD4+ T cells would be sensitive to $O_3$ exposure, but not LGM2605 treatment, based on our discoveries related to the ILC2 and CD123+ pDC response to $O_3$. We defined T cells derived from the peripheral blood and BAL as follows: T cells were gated as live CD45+CD3+ cells; CD4+ T cells were gated as CD4+CD8− T cells; CD8+ T cells were gated as CD4−CD8+ T cells (FIG. 15). We discovered that the proportion of BAL CD8+ T cells significantly increased in LGM2605+ air and placebo+$O_3$ animals, but not LGM2605+$O_3$ animals (FIG. 8A). The proportion of BAL CD4+ T cells was not significantly changed after LGM2605 treatment or $O_3$ exposure. Interestingly, when we calculated the absolute number of CD4+ and CD8+ T cells present in the BAL, we discovered that $O_3$ inhalation increased the number of CD4+, but not CD8+, T cells (FIGS. 8B-8C). This data was also visualized by parts of whole charts that reflect the favored CD4+ T cell environment in the airways after $O_3$ inhalation (FIG. 8D). We studied T cell activation by measuring the number of CD4+ and CD8+ T cells that were positive for CD25, a marker a T cell activation (40). We found that in response to $O_3$, the proportion of CD4+ T cells that expressed CD25 significantly increased (FIG. 8E). CD25 expression on BAL CD8+ T cells did not change in response to LGM2605 treatment or 03 inhalation (data not shown). In the peripheral blood, the proportion of CD8+ T cells in LGM2605+ air and placebo+$O_3$ animals increased, while this population was unchanged in LGM2605+$O_3$ animals (FIG. 16A). However, the absolute number of circulating CD4+ and CD8+ T cells in the blood was unchanged in response to LGM2605 treatment or $O_3$ exposure (FIGS. 16B-16C). CD25 expression was very low on blood T cells compared to BAL T cells, and did not significantly changed in circulating CD4+ or CD8+ T cells in response to LGM2605 treatment or $O_3$ exposure (FIG. 16D). Together, this data demonstrates that CD4+ T cells in the airways were sensitive to $O_3$ inhalation, independent of LGM2605 treatment.

LGM2605 Treatment Suppressed 03-Induced Destruction and De-Oligomerization of BAL SP-D.

Surfactant protein-D (SP-D) is a pulmonary immunoregulatory protein that is induced by inflammation as a negative feedback mechanism. Termed a collectin, SP-D is a large protein complex comprised of twelve monomers; each monomer contains a carbohydrate recognizing lectin head and collagenous tail. As an immunoregulatory protein, the function is SP-D is to act as a pattern recognition receptor, opsonizing inhaled pathogens, but also to suppress the function of innate and adaptive immune cells in the lung like ILC2s, DCs, and T cells. The protein structure of SP-D is critical to its anti-inflammatory functions. Indeed, induction of oxidative stress in the lung causes SP-D nitrosylation, which de-oligomerizes the protein and destroys its quaternary structure. Loss of SP-D quaternary structure impairs its ability to act as an immunosuppressive protein. Studies from our laboratory have indicated that SP-D acts as an immunosuppressive agent on lung ILC2s, DCs, and T cells [including unpublished]. Mice lacking SP-D expression were highly susceptible to $O_3$-induced neutrophilic inflammation. Taken together, this data demonstrates that expression of SP-D is necessary to limit the inflammatory response to inhaled $O_3$, and that de-oligomerization of SP-D heightens inflammation. Thus, we hypothesized that $O_3$ and LGM2605 increase expression of SP-D, but oxidative stress induced by $O_3$ inhalation causes de-oligomerization of SP-D, thus impairing its immunosuppressive effects on immune cells. We studied SP-D expression in the BAL before and after LGM2605 treatment and $O_3$ exposure. Reducing-PAGE western blots were used to examine total SP-D levels in the BAL, while native-PAGE western blots were used to examine de-oligomerization of SP-D in the BAL.

Figures 9A, 9B, 9C, 9D, 9E, 9F, 9G, 9H:
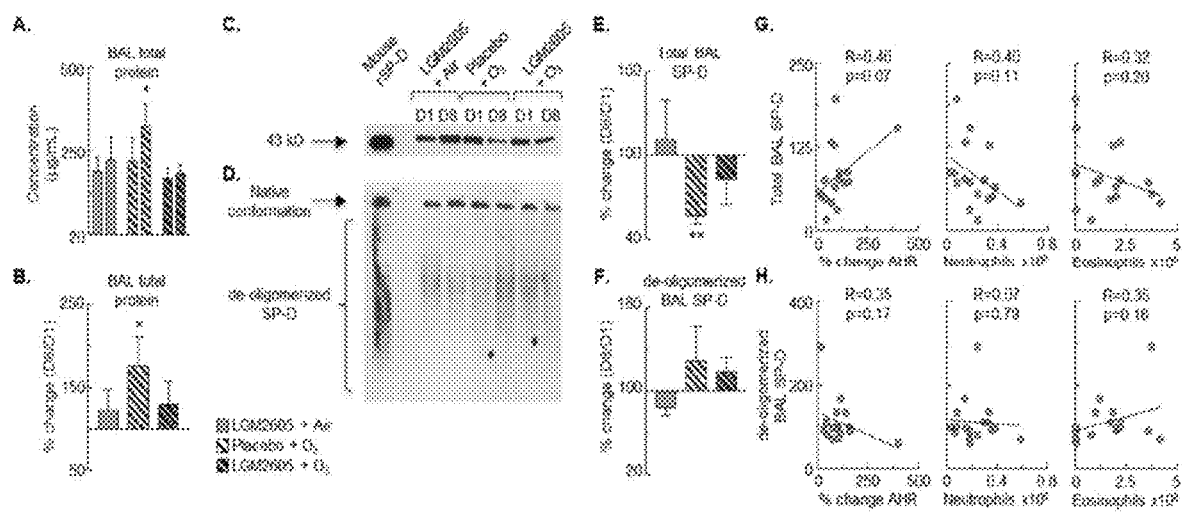
FIGS. 9A-9H illustrate that LGM2605 treatment suppressed $O_3$-induced destruction and de-oligomerization of BAL SP-D.

Total protein in the BAL was measured on day 1 and day 8 so that equal protein was studied in the western blot experiments. Consistent with the AHR inflammation induced in the placebo+$O_3$ group, we saw increased BAL total protein in this group that was inhibited by treatment with LGM2605 (FIGS. 9A-9B). BAL protein was studied via western blot for SP-D. A representative reducing-PAGE blot demonstrates that $O_3$ exposure significantly reduced total BAL SP-D, while LGM2605 treatment prevent such change (FIG. 9C). In fact, LGM2605 treatment followed by air exposure caused a trend for increase in total SP-D expression (FIG. 9C). These results were confirmed by semi-quantitative densitometry analysis via ImageJ (FIG. 9E). De-oligomerization and destruction of the quaternary structure of SP-D was studied via a native-PAGE western blot. A representative blot shows a trend for de-oligomerization in rhesus exposed to $O_3$ (FIG. 9D). Semi-quantitative densitometry analysis via ImageJ revealed a trend in $O_3$-induced SP-D de-oligomerization that could be partially inhibited by LGM2605 treatment, although such changes were not statistically significant (FIG. 9F). Correlations were drawn between total SP-D (reducing blots) and SP-D structure (native blots) against percent change in AHR, BAL neutrophilia, and BAL eosinophilia. None of these correlations were statistically significant (FIGS. 9G-9H). Together this data suggest that $O_3$ impairs SP-D expression and that LGM2605 can partially reverse this adverse effect. While $O_3$ may cause some de-oligomerization of SP-D, our data suggests that instead it completely destroys the immunoprotective protein.

LGM2605 Protected from $O_3$-Induced IL-5 in the BAL.

Figure 10:
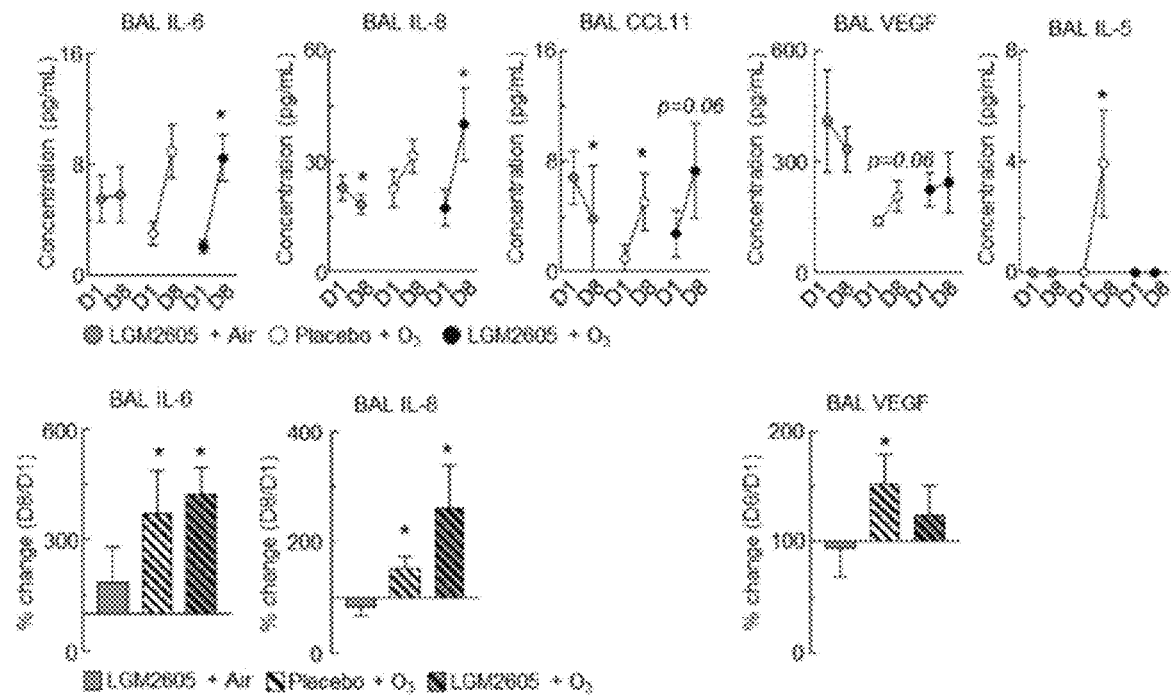
FIG. 10 illustrates that LGM2605 protected from $O_3$-induced IL-5, but not IL-6, IL-8, CCL11, and VEGF in the BAL. Cytokines and chemokines were measured in the BAL via Luminex assay. As appropriate, percent change from day 1 to day 8 was calculated so that each animal served as its own control.

$O_3$ exposure caused a marked increase in AHR that was prevented by LGM2605, while eosinophilic and neutrophilic inflammation was reduced by LGM2605. We investigated how cytokine and chemokine mediators that are related to AHR and inflammation changed in the BAL and serum in response to LGM2605 and $O_3$. IL-6 and IL-8 were measured as they are key mediators of neutrophilic inflammation in response to $O_3$, while CCL11 and IL-5 were measured as key mediators of eosinophilic inflammation, and VEGF was shown to regulate AHR in response to IL-33 activation of ILC2s. Interestingly, we found that BAL IL-6, IL-8, and CCL11 was increased in response to $O_3$ inhalation but not affected by LGM2605 treatment (FIG. 10). BAL IL-5 and VEGF on the other hand were significantly increased in response to $O_3$ and LGM2605 prevented such an increase (FIG. 10). This suggests that expression of these cytokines from airway epithelial cells (VEGF) or inflammatory cells such as ILC2s (VEGF, IL-5) impacts the inflammatory and functional response of the lung to $O_3$.

Conclusions: In this study, the following was shown: (1) $O_3$ induced AHR, BAL neutrophilia, and BAL eosinophilia in rhesus macaques (2) LGM2605 completely abolished AHR caused by $O_3$ inhalation (3) LGM2605 significantly reduced $O_3$-induced BAL neutrophilia but not eosinophilia (4) LGM2605 protected from ozone-induced IL-6, IL-25, IL-33, and CCL11 gene expression in airway epithelial cells derived from lung brushings (5) ILC2, CD1c+ mDC, CD123+ pDC, and CD4+ T cell immunity was enhanced by O₃ inhalation. There was a trend for reduction of BAL ILC2 and CD1c+ mDC numbers by LGM2605 treatment in response to O₃. (6) O₃ reduced mRNA expression of GATA3, IL-13, and IL-17A in isolated blood ILC2s, while LGM2605 treatment prevented these changes. Together, the present data on AHR and BAL inflammation support the findings of other studies conducted in mouse models and in rhesus macaques. The following has been found: These studies were the first to identify ILC subsets in rhesus airways. A significant anti-inflammatory benefit of oral LGM2605 was demonstrated in response to an environmentally relevant dose of O₃ exposure. The protective effect of LGM2605 against airway hyperreactivity was disproportionately greater than against airway inflammation indicating a special benefit of this compound in the treatment of asthma.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

All publications, accession numbers, patents, and patent applications cited in this specification are herein incorporated by reference as if each was specifically and individually indicated to be incorporated by reference.

What is claimed is:

1. A method for treating ozone-induced damage in a biomolecule, a cell, or a tissue of a subject in need thereof, the method comprising: administering to the subject a therapeutically effective amount of chemically synthesized SDG, wherein the biomolecule, the cell, or the tissue is located in a respiratory airway of the subject.

2. The method of claim 1, wherein the chemically synthesized SDG comprises a racemic mixture of the SDG.

3. The method of claim 1, wherein administration of the chemically synthesized SDG alleviates or eliminates respiratory airway hyperactivity in the subject.

4. The method of claim 3, wherein the respiratory airway is an upper respiratory airway, a lower respiratory airway or a combination thereof.

5. The method of claim 1, wherein administration of the chemically synthesized SDG alleviates or eliminates BAL inflammation in the subject.

6. The method of claim 5, wherein alleviation or elimination of the BAL inflammation comprises reducing ozone-induced BAL neutrophilia.

7. The method of claim 1, wherein administration of the chemically synthesized SDG alleviates or eliminates oxidative stress.

8. The method of claim 1, wherein the chemically synthesized SDG inhibits surfactant protein-D (SP-D) de-oligomerization.

9. The method of claim 1, wherein the chemically synthesized SDG protects the biomolecule, the cell, or the tissue from ozone-induced IL-6, IL-25, IL-33, and CCL11 gene expression in respiratory airway epithelial cells.

10. The method of claim 1, wherein the chemically synthesized SDG reduces BAL group 2 innate lymphoid cells (ILC2) and CD1c+mDC dendritic cells in the respiratory airway of the subject.

11. The method of claim 1, wherein the subject is one who will be exposed to ozone.

12. The method of claim 1, wherein the subject is one who has been exposed to ozone.

13. The method of claim 1, wherein the subject is a human subject.

14. The method of claim 1, wherein the chemically synthesized SDG is administered in a dietary composition.

15. The method of claim 1, wherein the chemically synthesized SDG is administered orally.

16. A method for protecting a biomolecule, a cell, or a tissue from ozone-induced damage in a subject in need thereof, the method comprising: administering to the subject therapeutically effective amount of at least one bioactive ingredient, wherein the bioactive ingredient comprises a therapeutically effective amount of chemically synthesized SDG.

17. The method of claim 16, wherein the chemically synthesized SDG comprises a racemic mixture of the SDG.

18. The method of claim 16, wherein the biomolecule is a nucleic acid.

19. The method of claim 16, wherein the biomolecule is a protein or a lipid.

20. The method of claim 16, wherein the chemically synthesized SDG is an SDG analog.

21. The method of claim 16, wherein the chemically synthesized SDG is administered in a dietary composition.

22. The method of claim 16, wherein said step of administering comprises orally administering.

23. The method of claim 16, wherein the chemically synthesized SDG is in a concentration about 1 nanomolar (nM) to about 1 molar (M).

24. The method of claim 23, wherein the SDG concentration is about 25 µM to about 250 µM.

25. The method of claim 16, wherein the subject is a human subject.

* * * * *